United States Patent
Tsourkas et al.

(10) Patent No.: US 12,270,809 B2
(45) Date of Patent: *Apr. 8, 2025

(54) METHOD FOR THE SITE-SPECIFIC COVALENT CROSS-LINKING OF ANTIBODIES TO SURFACES

(71) Applicant: THE TRUSTEES OF THE UNIVERSITY OF PENNSYLVANIA, Philadelphia, PA (US)

(72) Inventors: Andrew Tsourkas, Bryn Mawr, PA (US); James Z Hui, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 47 days.

This patent is subject to a terminal disclaimer.

(21) Appl. No.: 17/508,742

(22) Filed: Oct. 22, 2021

(65) Prior Publication Data

US 2022/0214337 A1 Jul. 7, 2022

Related U.S. Application Data

(63) Continuation of application No. 14/774,883, filed as application No. PCT/US2014/030457 on Mar. 17, 2014, now Pat. No. 11,156,608.

(Continued)

(51) Int. Cl.
*G01N 33/543* (2006.01)
*A61K 47/62* (2017.01)
(Continued)

(52) U.S. Cl.
CPC ....... *G01N 33/54353* (2013.01); *A61K 47/62* (2017.08); *A61K 47/65* (2017.08);
(Continued)

(58) Field of Classification Search
CPC ........... G01N 33/54353; G01N 33/582; A61K 47/62; A61K 47/65; A61K 47/6855;
(Continued)

(56) References Cited

U.S. PATENT DOCUMENTS

| | | |
|---|---|---|
| 3,773,919 A | 11/1973 | Boswell et al. |
| 4,485,045 A | 11/1984 | Regen |

(Continued)

FOREIGN PATENT DOCUMENTS

| | | |
|---|---|---|
| WO | WO 1997/38731 | 10/1997 |
| WO | WO 2005/051976 | 6/2005 |

(Continued)

OTHER PUBLICATIONS

Cedergren et al., "Mutational analysis of the interaction between staphylococcal protein A and human IgG1." Protein Engineering, vol. 6(4); pp. 441-448, Jun. 1993.

(Continued)

*Primary Examiner* — Shafiqul Haq
*Assistant Examiner* — Nam P Nguyen
(74) *Attorney, Agent, or Firm* — Mark S. Cohen; PEARL COHEN ZEDEK LATZER BARATZ LLP

(57) ABSTRACT

This invention relates to conjugate antibody, drug and nanoparticle compositions and methods of generating the same. This invention further relates to methods of using same for imaging, diagnosing or treating a disease.

25 Claims, 24 Drawing Sheets

Specification includes a Sequence Listing.

Related U.S. Application Data

(60) Provisional application No. 61/800,926, filed on Mar. 15, 2013.

(51) Int. Cl.
*A61K 47/65* (2017.01)
*A61K 47/68* (2017.01)
*A61K 49/18* (2006.01)
*C07K 14/31* (2006.01)
*C07K 17/00* (2006.01)
*C07K 17/06* (2006.01)
*G01N 33/58* (2006.01)

(52) U.S. Cl.
CPC ...... *A61K 47/6855* (2017.08); *A61K 49/1875* (2013.01); *C07K 14/31* (2013.01); *C07K 17/00* (2013.01); *C07K 17/06* (2013.01); *G01N 33/582* (2013.01); *C07K 2319/30* (2013.01)

(58) Field of Classification Search
CPC .... A61K 49/1875; C07K 14/31; C07K 17/00; C07K 17/06; C07K 2319/30
See application file for complete search history.

(56) References Cited

U.S. PATENT DOCUMENTS

| | | | |
|---|---|---|---|
| 4,544,545 | A | 10/1985 | Ryan et al. |
| 5,013,556 | A | 5/1991 | Woodle et al. |
| 8,916,689 | B2 | 12/2014 | Hober et al. |
| 11,156,608 | B2 * | 10/2021 | Tsourkas ............... C07K 17/06 |
| 2003/0082575 | A1 | 5/2003 | Schultz et al. |
| 2014/0249296 | A1 | 9/2014 | Ploegh et al. |
| 2016/0032346 | A1 | 2/2016 | Tsourkas et al. |

FOREIGN PATENT DOCUMENTS

| | | |
|---|---|---|
| WO | WO 2012/033446 | 3/2012 |
| WO | WO 2014/145441 | 9/2014 |
| WO | WO 2014/145654 | 9/2014 |

OTHER PUBLICATIONS

Chari et al., "Immunoconjugates containing novel maytansinoids: promising anticancer drugs", Cancer Research 1992,52: 127-131.

Elias et al., "An Intein-Medicated Site-Specific Click Conjugation Strategy for Improved Tumor Targeting of Nanoparticle Systems". Small 2010, Nov. 5, vol. 6 (21), pp. 2460-2468.

Eppstein et al., "Biological activity of liposome-encapsulated murine interferon gamma is mediated by a cell membrane receptor", Proc. Natl. Acad. Sci. 1985, 82:3688.

Gabizon et al., "Pharmacokinetics and tissue distribution of doxorubicin encapsulated in stable liposomes with long circulation times", J. National Cancer Inst. 1989,81: 1484.

Guo et al, "Protein tolerance to random amino acid change" 2004, Proc. Natl. Acad. Sci. USA 101: 9205- 9210. (Year: 2004).

Hui et al., Facile Method for the site-specific, covalent attachment of full-length IgG onto nanoparticles, Small 2014, pp. 1-10.

Hui et al., "Optimization of photoactive protein Z for the fast and efficient site-specific conjugation of native IgG." Aug. 2014. 27:; 25(9): 1709-19.

Hwang et al., "Hepatic uptake and degradation of unilamellar sphingomyelin/cholesterolliposomes: a kinetic study", Proc. Natl. Acad. Sci. 1980, 77:4030.

Perols et al., "Stite-specific photoconjugation of antibodies using chemically synthesized IgG-binding domains". Bioconjugate chemistry. Feb. 25, 2014;25(3):481-8.

Rudikoff et al., "Single amino acid substitution altering antigenbinding specificity" Proc Natl Acad Sci USA vol. 79 pp. 1979-1983 (Year: 1982).

Stahl et al., "The use of gene fusions to protein A and protein G in immunology and biotechnology", Pathol. Biol. 1997, vol. 45, No. 1, pp. 66-76.

Stella et al., "Prodrugs: A Chemical Approach to Targeted Drug Delivery", in Directed Drug Delivery, Borchardt et al., 247-267, Humana Press 1985.

Wagner et al., "Bispecific antibody generated with sortase and click chemistry has broad antiinfluenza virus activity." Proceedings of he National Academy of Sciences. Nov. 25, 2014;111(47):16820-5.

Willman, "Biochemical Society Transactions, 1986, 615" Meeting Belfast, 14: 375-382.

\* cited by examiner

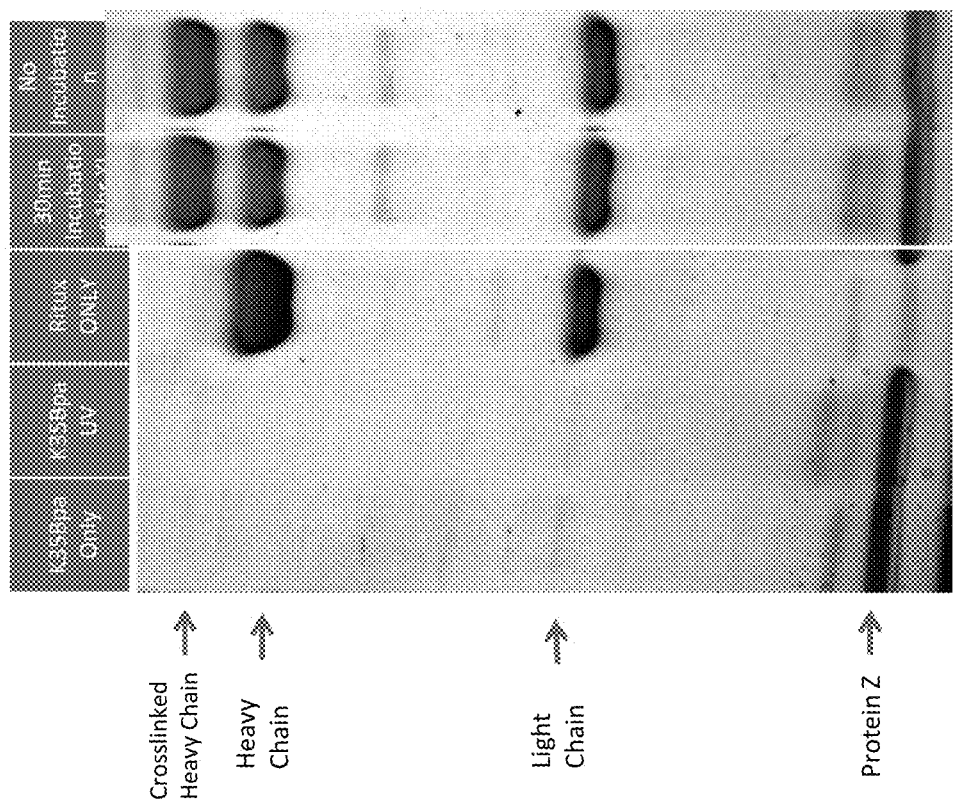

Site of Crosslinking

Crosslinked Heavy Chain
Heavy Chain
Light Chain

FIGURE 26A
FIGURE 26B
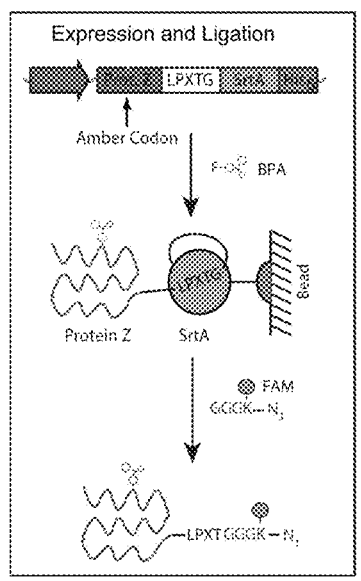
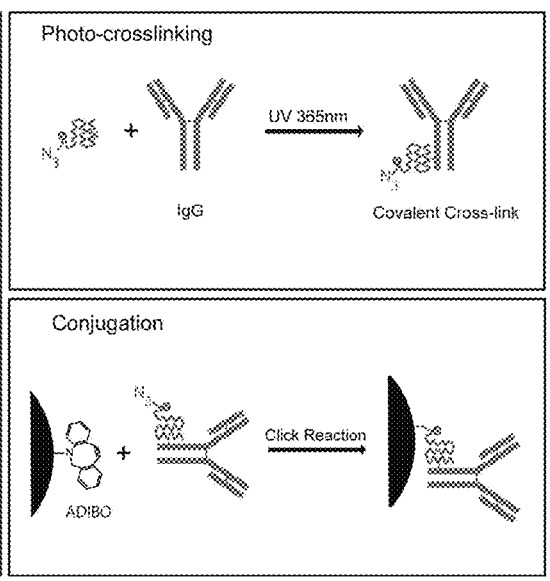
FIGURE 26C

SEQUENCE LISTING

```
<160> NUMBER OF SEQ ID NOS: 1

<210> SEQ ID NO 1
<211> LENGTH: 61
<212> TYPE: PRT
<213> ORGANISM: Staphylococcus aureus

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Met Arg Met
    50                  55                  60
```

METHOD FOR THE SITE-SPECIFIC COVALENT CROSS-LINKING OF ANTIBODIES TO SURFACES

CROSS-REFERENCE TO RELATED APPLICATIONS

This application is a Continuation of U.S. application Ser. No. 14/774,883, filed Sep. 11, 2015, which is a National Phase Application of PCT International Application No. PCT/US14/30457, International filing date Mar. 17, 2014, which claims priority to and the benefit of U.S. Provisional Patent Application 61/800,926, filed Mar. 15, 2013, each of which are which is incorporated by reference herein its entirety.

GOVERNMENT INTEREST STATEMENT

This invention was made with government support under grant numbers EB012065 and CA157766 awarded by the National Institutes of Health. The United States government has certain rights in the invention.

FIELD OF THE INVENTION

The invention relates to conjugate antibody, drug and nanoparticle compositions and methods of generating the same. This invention further relates to methods of using same for imaging, diagnosing or treating a disease.

BACKGROUND OF THE INVENTION

There exist a wide range of both site specific and non-site specific conjugation methods. The most popular bioconjugation methods involve non-site specific attachment of antibodies through exposed amine groups. These methods are problematic as there are amine groups distributed throughout the antibody, hence a large proportion of conjugated antibodies are sterically-hindered around their Fab region and do not function properly. Additionally, inter-IgG cross-linking can occur with many of these methods, creating a heterogeneous mix of antibody aggregates that requires subsequent separation. Therefore these methods are inefficient, costly, and produce conjugates that often have lower functional activities.

Other methods also exist that utilize some special chemical groups that only occur in some IgGs or engineered IgGs to achieve site-specific linkage. Such groups include carbohydrate molecules found in some post-transnationally modified IgGs and cysteine residues that are deliberately engineered into recombinantly produced IgGs, a procedure that's costly and lengthy. These conjugation methods therefore, are only available to a small subset of IgG molecules, while our conjugation method is applicable to nearly all IgG molecules.

Recent work showed that a conserved nucleotide binding site (NBS) can be used to conjugate a range of IgG molecules. However, the proximity of this NBS to Fab would decrease the functional activity of conjugated IgGs. Additionally, this method requires exposures to short-wavelength UV (250 nm), which damages proteins including antibodies, further lowering the functional activities of the resulting conjugates.

Protein Z variants that incorporated BPAs and can be cross-linked onto IgG with UV exposure have been prepared. However, these Protein Z variants were produced by peptide synthesis, which is considerably more costly and less scalable than our recombinant method. Additionally, the reported best variant Phe5BPA only showed a modest amount of cross-linking to a small subset of IgG's (e.g. not mouse IgG1 and rat IgG) in our experiment and exhibited short activity half-life due to possible intramolecular cross-linking. Moreover, this peptide synthesis based method is not well suited for the production of protein fusions, since synthetic methods are much more limited than recombinant methods in producing larger proteins and fusions, especially if the proteins involved have complex secondary structures. As discussed above, this is important when it is desirable to site-specifically attach protein/peptide-based drugs to antibody. Lastly, no previous study discloses the addition of click chemistry groups to the C-terminus.

There is a need for optimal site-selective conjugation methods. The present invention addresses this need by providing conjugation methods without evidence of intramolecular cross-linking.

SUMMARY OF THE INVENTION

In one embodiment, the invention relates to a conjugate composition comprising a recombinant protein comprising an amino acid that permits specific binding to an immunoglobulin Fc region.

In one embodiment, the invention relates to a conjugate composition comprising a recombinant protein, wherein said protein comprises an amino acid that permits specific binding to an immunoglobulin Fc region, wherein said protein comprises a moiety for expressed protein ligation (EPL), wherein said composition further comprises a peptide comprising a moiety for click chemistry.

In another embodiment, the invention relates to a method of producing a conjugate composition comprising a recombinant protein, wherein said protein comprises an amino acid that permits specific binding to an immunoglobulin Fc region, wherein said protein comprises a moiety for expressed protein ligation (EPL), wherein said composition further comprises a peptide comprising a moiety for click chemistry, the method comprising the step of recombinantly expressing said recombinant protein and conjugating said recombinant protein to said peptide via said EPL.

In another embodiment, the invention relates to a conjugate composition comprising: an IgG binding recombinant protein, said IgG binding protein comprising a photoactive moiety capable of crosslinking IgG (e.g., moiety comprising benzoylphenylalanine), a moiety capable of mediating a click reaction for functionalization (e.g., an azido moiety), and a detection agent (e.g., a fluorophore).

In another embodiment, the invention relates to a method of producing a conjugate composition comprising, said conjugate composition: an IgG binding recombinant protein, said IgG binding protein comprising a photoactive moiety capable of crosslinking IgG (e.g., moiety comprising benzoylphenylalanine), a moiety capable of mediating a click reaction for functionalization (e.g., an azido moiety), and a detection agent (e.g., a fluorophore).

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 20 shows that no Pre-incubation is needed for crosslinking with K35BPA of Protein Z.

FIG. 25A shows $Z_{K35Bpa}$-GGSX7-$Z_{K35Bpa}$ dimer showing self aggregation and high molecular aggregates. FIG. 25B shows $Z_{WT}$-GGSX7-$Z_{Q32Bpa}$ dimer showing WT Protein Z domain competing with Q32Bpa domain for binding to IgG.

FIGS. 26A-26C Schematic describing one method for the production and surface conjugation of Protein Z-IgG complexes. Protein Z is produced in an entirely recombinant manner (FIG. 26A). This is achieved by using *E. coli* that have been engineered to incorporate the unnatural amino acid, BPA, into proteins during translation. A sortase-mediated Expressed Protein Ligation (EPL) technique can be used to ligate peptides to the carboxy-terminus of recombinant proteins during the affinity purification process. This sortase-mediated EPL technique is described in greater detail in U.S. provisional Appl. No. 61/799,379 (filed on Mar. 15, 2013) and in co-pending PCT Application No. PCT/US2014/030208 entitled "Sortase-Mediated Protein Purification And Ligation" (filed on Mar. 17, 2014), both applications are hereby incorporated in their entirety. Many functionalities can be included on this peptide, including crosslinking groups (azide/alkyne, biotin, maleimide) imaging agents (fluorophores, radionuclides), drugs or any combination thereof. The Protein Z-peptide conjugate can be photocrosslinked to IgG (FIG. 26B). Azide-modified IgG-Protein Z-peptide conjugates can be efficiently conjugated to any surface functionalized with an alkyne (FIG. 26C).

DETAILED DESCRIPTION OF THE INVENTION

Figure 1:
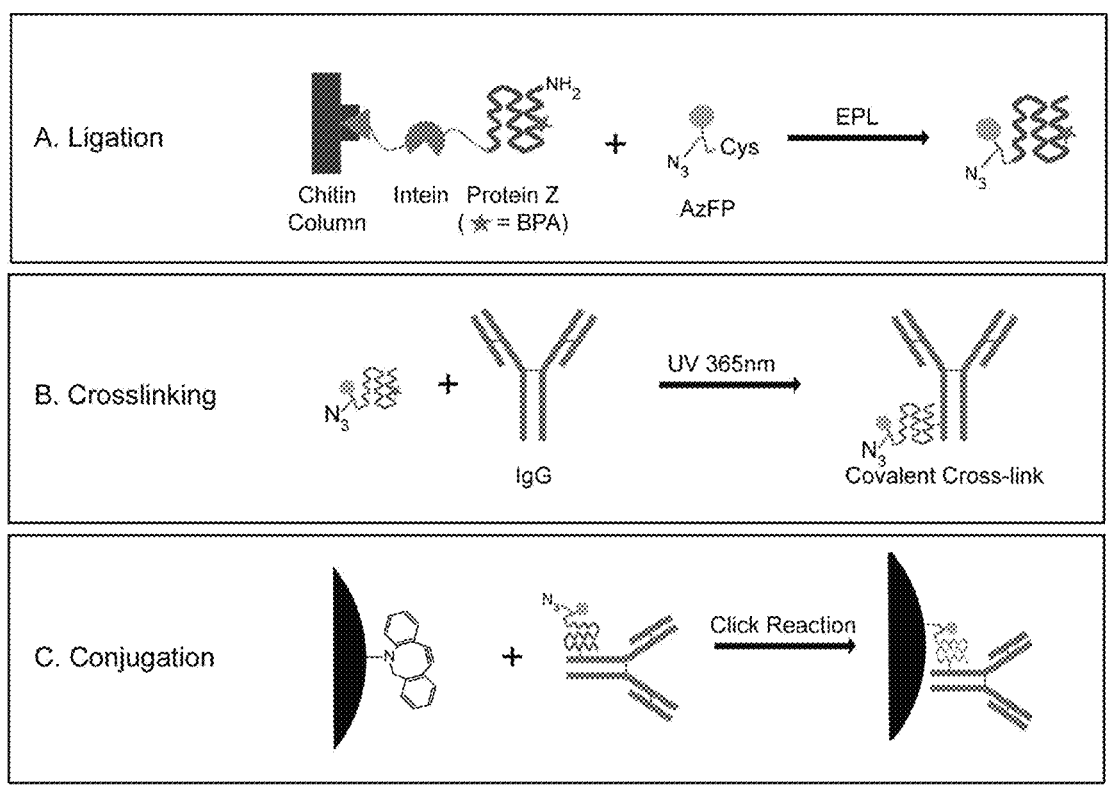
FIG. 1. Schematic describing the production and surface conjugation of Protein Z-IgG complexes. (A) A fusion protein containing an unnatural amino acid benzoylphenylalanine (EPA) in the Protein Z domain is expressed in frame with an intein and a chitin binding domain. During the affinity purification process, the intein is used to drive expressed protein ligation between the Protein Z and an azido fluorescent peptide (AZFP) containing an N-terminal cysteine, a "clickable" azide group and a 5-FAM fluorophore. (B) After the protein Z-AZFP conjugate is mixed with IgG, long-wavelength UV irradiation is used to create a site-specific FIG. 1. Schematic describing the production and surface conjugation of Protein Z-IgG complexes. (A) A fusion protein containing an unnatural amino acid benzoylphenylalanine (BPA) in the Protein Z domain is expressed in frame with an intein and a chitin binding domain. During the affinity purification process, the intein is used to drive expressed protein ligation between the Protein Z and an azido fluorescent peptide (AzFP) containing an N-terminal cysteine, a "clickable" azide group and a 5-FAM fluorophore. (B) After the protein Z-AzFP conjugate is mixed with IgG, long-wavelength UV irradiation is used to create a site-specific covalent bond between the BPA and Fc region of IgG. (C) The crosslinked IgG, now containing both a fluorophore and an azide moiety, can be used for site-specific conjugation with any substrate containing a free alkyne via click chemistry. A strained alkyne, aza-dibenzocyclooctyne (ADIBO), capable of copper-free click reactions is shown.

In one aspect provided herein, the invention relates to a conjugate composition comprising a recombinant protein comprising an amino acid that permits specific binding to an immunoglobulin Fc region.

In another aspect, provided herein is a conjugate composition comprising a recombinant protein, wherein said protein comprises an amino acid that permits specific binding to an immunoglobulin Fc region, wherein said protein comprises a moiety for expressed protein ligation (EPL), and wherein said composition further comprises a peptide comprising a moiety for click chemistry.

In one embodiment, the immunoglobulin is IgG.

In another embodiment, the recombinant protein is a recombinant bacterial protein. In another embodiment, the recombinant bacterial protein is Protein Z.

The term "Protein Z," as used herein, may refer to the Z domain based on B domain of Staphylococcal aureus Protein A. The amino acid sequence of Protein Z is: VDNKFNKEQQNAFYEILHLPNLNEEQR-NAFIQSLKDDPS QS ANLLAEAKKLNDAQAP KMRM (SEQ ID NO: 1). The amino acid sequence of Protein Z may also include homologous, variant, and fragment sequences having Z domain function. In some embodiments, the amino acid sequence of Protein Z may include an amino acid sequence which is 60, 65, 70, 75, 80, 85, 90, 95, or 99% identity to the sequence set forth in SEQ ID NO: 1.

In another embodiment, the recombinant protein is a fusion protein. In another embodiment, the fusion protein comprises Protein Z and an additional polypeptide. In one embodiment, the recombinant protein further comprises a moiety for expressed protein ligation. In another embodiment, the moiety is an intein-MPB group or a sortase-His×6 group. In another embodiment, the recombinant protein is attached to a peptide via expressed protein ligation.

In one embodiment, peptide attached to the recombinant protein is attached to an additional polypeptide of interest via a crosslinker. In another embodiment, the additional polypeptide is a drug or a toxin.

In one embodiment, the peptide comprises a chemical moiety that permits chemical binding to a corresponding chemical group. In another embodiment, the chemical binding occurs via click chemistry or maleimide. In another embodiment, the recombinant protein is site-specifically attached in the proper orientation to a surface, a polypeptide, a nanoparticle, or a drug.

In one embodiment, provided herein is a bacterial cell for recombinantly expressing the composition provided herein. In another embodiment, the bacterial cell is for recombinantly expressing the recombinant protein provided herein. In another embodiment, the recombinant protein is Protein Z, Protein A or Protein G.

In one embodiment, the conjugate composition provided herein is a nanoparticle conjugate composition comprising a nanoparticle conjugated to Protein Z via EPL or click chemistry. In another embodiment, the conjugate composition provided herein is a nanoparticle conjugate composition comprising a nanoparticle conjugated to an antibody via EPL and to Protein Z via click chemistry.

In one embodiment, provided herein is a conjugate composition comprising a modified antibody complex. In another embodiment, the conjugate composition comprises an antibody conjugated to Protein Z via a UV-activated covalent bond. In another embodiment, the covalent bond between Protein Z and the antibody is possible because of an amino acid on Protein Z. In another embodiment, the amino acid is a UV-active non-natural amino acid. In another embodiment, amino acid is benzoylphenylalaine (BPA). Other suitable photoactive moiety capable of crosslinking IgG, known to one of skilled in the art, can also be used.

In one embodiment, a mutation is made in IgG binding protein (e.g., Protein Z) in order to include a photoactive moiety. For example, one or more amino acid residues in Protein Z can be replaced with a photoactive moiety. In a particular embodiment, one or more mutations are made in Protein Z to include BPA. Examples of BPA-containing mutants of Protein Z include, for example, but are not limited to, F13BPA, F5BPA, Q32BPA, K35BPA, N28BPA, N23BPA, and L17BPA. The mutants can be created by replacing the respective amino acid residues with BPA.

In one embodiment, provided herein is a conjugate composition comprising a modified antibody complex. In another embodiment, the conjugate composition comprises an antibody conjugated to Protein Z via a UV-activated covalent bond and a peptide of interest conjugated to Protein Z via EPL. In another embodiment, the conjugate composition comprises an antibody conjugated to Protein Z via a UV-activated covalent bond, a peptide of interest conjugated to Protein Z via EPL. In another embodiment, the peptide comprises an azide group for click chemistry. In another embodiment, said azide group permits binding of the conjugate composition to a surface, a drug, a polypeptide or a nanoparticle.

In one embodiment, provided herein is a method of imaging a biological sample, the method comprising the step of contacting said biological sample with the nanoparticle conjugate, wherein said contacting permits imaging of said biological sample.

In another embodiment is a method of imaging a biological sample, the method comprising the step of contacting a biological sample with said conjugate comprising said antibody complex, wherein said contacting permits imaging of said biological sample.

In one aspect provided herein, the invention relates to a method of producing a conjugate composition comprising a recombinant protein, wherein said protein comprises an amino acid that permits specific binding to an immunoglobulin Fc region, wherein said protein comprises a moiety for expressed protein ligation (EPL), wherein said composition further comprises a peptide comprising a moiety for click chemistry, wherein the method comprising the step of recombinantly expressing said recombinant protein and conjugating said recombinant protein to said peptide via said EPL.

As used herein, the term immunoglobulin G or "IgG" refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. In another embodiment, the term "immunoglobulin (Ig)" refers to a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains.

As used herein, the term "Fc domain" encompasses the constant region of an immunoglobulin molecule.

The Fc region of an antibody interacts with a number of Fc receptors and ligands, imparting an array of important functional capabilities referred to as effector functions, as described herein. For IgG the Fc region comprises Ig domains CH2 and CH3. An important family of Fc receptors for the IgG isotype are the Fc gamma receptors (FcγRs). These receptors mediate communication between antibodies and the cellular arm of the immune system.

As used herein, the term "immunoglobulin G" or "IgG" refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. As used herein, the term "modified immunoglobulin G" refers to a molecule that is derived from an antibody of the "G" class. As used herein, the term "antibody" refers to a protein consisting of one or more polypeptides substantially encoded by all or part of the recognized immunoglobulin genes. The recognized immunoglobulin genes, for example in humans, include the kappa (κ) lambda (λ) and heavy chain genetic loci, which together comprise the myriad variable region genes, and the constant region genes mu (μ) delta (δ), gamma (γ), sigma (σ) and alpha (α) which encode the IgM, IgD, IgG, IgE, and IgA isotypes or classes, respectively. In another embodiment, the term "antibody" is meant to include full length antibodies, and may refer to a natural antibody from any organism, an engineered antibody, or an antibody generated recombinantly for experimental, therapeutic, or other purposes as further defined below. In another embodiment, full length antibodies comprise conjugates as described and exemplified herein. As used herein, the term "antibody" comprises monoclonal and polyclonal antibodies. Antibodies can be antagonists, agonists, neutralizing, inhibitory, or stimulatory. Specifically included within the definition of "antibody" are full-length antibodies described and exemplified herein. By "full length antibody" herein is meant the structure that constitutes the natural biological form of an antibody, including variable and constant regions.

The "variable region" of an antibody contains the antigen binding determinants of the molecule, and thus determines the specificity of an antibody for its target antigen. The variable region is so named because it is the most distinct in sequence from other antibodies within the same isotype. The majority of sequence variability occurs in the complementarity determining regions (CDRs). There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens.

It will be appreciated that the term "modification" can encompass an amino acid modification such as an amino acid substitution, insertion, and/or deletion in a polypeptide sequence.

In one embodiment, a variety of radioactive isotopes are available for the production of radioconjugate antibodies and can be of use in the methods and compositions provided herein. Examples include, but are not limited to, $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu.

In an alternate embodiment, enzymatically active toxin or fragments thereof that can be used in the compositions and methods provided herein include, but are not limited, to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

A chemotherapeutic or other cytotoxic agent may be conjugated to the recombinant protein, according to the methods provided herein, as a prodrug. The term "prodrug" refers to a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use with the compositions and methods as provided herein include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies and Fc fusions of the compositions and methods as provided herein include but are not limited to any of the aforementioned chemotherapeutic.

In one embodiment, any combination of the recombinant protein with the biological active agents specified above, i.e., a cytokine, an enzyme, a chemokine, a radioisotope, an enzymatically active toxin, or a chemotherapeutic agent can be applied.

In one embodiment, a variety of other therapeutic agents may find use for administration with the antibodies and conjugates of the compositions and methods provided herein. In one embodiment, the conjugate comprising an antibody is administered with an anti-angiogenic agent. As used herein, the term "anti-angiogenic agent" refers to a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. In an alternate embodiment, the conjugate is administered with a therapeutic agent that induces or enhances adaptive immune response. In an alternate embodiment, the conjugate is administered with a tyrosine kinase inhibitor. The term "tyrosine kinase inhibitor" refers to a molecule that inhibits to some extent tyrosine kinase activity of a tyrosine kinase as known in the art.

In one embodiment, the conjugates provided herein may be used for various therapeutic purposes. In one embodiment, the conjugates are administered to a subject to treat an antibody-related disorder. In another embodiment, the conjugate proteins are administered to a subject to treat a tumor or a cancer tumor. A "subject" for the purposes of the compositions and methods provided herein includes humans and other animals, preferably mammals and most preferably humans. Thus the conjugates provided herein have both human therapy and veterinary applications. In another embodiment the subject is a mammal, and in yet another embodiment the subject is human By "condition" or "disease" herein are meant a disorder that may be ameliorated by the administration of a pharmaceutical composition comprising the conjugate of the compositions and methods provided herein. Antibody related disorders include but are not limited to autoimmune diseases, immunological diseases, infectious diseases, inflammatory diseases, neurological diseases, and oncological and neoplastic diseases including cancer.

In another embodiment, provided herein is a nucleic acid construct encoding the conjugate provided herein. In some embodiments, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, provided herein are primers used for amplification and construction of the vectors and nucleic acids provided herein. It is to be understood by a skilled artisan that other primers can be used or designed to arrive at the vectors, nucleic acids and conjugates provided herein.

In one embodiment, provided herein is a vector comprising the nucleic acid encoding for the conjugate components provided herein. In another embodiment, the vector comprises nucleic acid encoding the recombinant protein, polypeptides, peptides, antibodies, and recombinant fusions provided herein.

In another embodiment, the nucleic acid can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include any culture conditions which are suitable for achieving production of the polypeptide by the host cell, including effective temperatures, pH, medusa, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. In another embodiment, a nucleic acid can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which the nucleic acid provided herein has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells (e.g., COS-7, CV1, BHK, CHO, HeLa, LTK, NIH 3T3, 293, PAE, human, human fibroblast, human primary tumor cells, testes cells), insect cells, such as Sf9 (S. frugipeda) and Drosophila, bacteria, such as E. coli, Streptococcus, bacillus, yeast, such as S. cerevisiae (e.g., cdc mutants, cdc25, cell cycle and division mutants, such as ATCC Nos. 42563, 46572, 46573, 44822, 44823, 46590, 46605, 42414, 44824, 42029, 44825, 44826, 42413, 200626, 28199, 200238, 74155, 44827, 74154, 74099, 201204, 48894, 42564, 201487, 48893, 28199, 38598, 201391, 201392), fungal cells, plant cells, embryonic stem cells (e.g., mammalian, such as mouse or human), fibroblasts, muscle cells, neuronal cells, etc. Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, promoters of other genes in the cell signal transduction pathway, MMTV, SV40, trp, lac, tac, or T7 promoters for bacterial hosts; or alpha factor, alcohol oxidase, or PGH promoters for yeast.

In one embodiment, reporter genes may be incorporated within expression constructs to facilitate identification of transcribed products. Accordingly and in one embodiment of the compositions and methods provided herein, reporter genes utilized are selected from the group consisting of β-galactosidase, chloramphenicol acetyl transferase, luciferase and a fluorescent protein.

In one embodiment, the conjugates are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of conjugates. For example, the bacterial proteins A and G bind to the Fc region. Likewise, the bacterial protein L binds to the Fab region of some antibodies, as of course does the antibody's target antigen. Purification can often be enabled by a particular fusion partner. For example, proteins may be purified using glutathione resin if a GST fusion is employed, $Ni^{+2}$ affinity chromatography if a His-tag is employed, or immobilized anti-flag antibody if a flag-tag is used. The degree of purification necessary will vary depending on the screen or use of the conjugates. In some instances no purification is necessary. For example in one embodiment, if the conjugates are secreted, screening may take place directly from the media. As is well known in the art, some methods of selection do not involve purification of proteins. Thus, for example, if a library of conjugates is made into a phage display library, protein purification may not be performed.

Conjugates may be screened using a variety of methods, including but not limited to those that use in vitro assays, in vivo and cell-based assays, and selection technologies. Automation and high-throughput screening technologies may be utilized in the screening to procedures. Screening may employ the use of a fusion partner or label. The use of fusion partners has been discussed above. By "labeled" herein is meant that the conjugates of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of conjugates are screened in an in vitro assay. In vitro assays may allow a broad dynamic range for screening properties of interest. Properties of conjugates that may be screened include but are not limited to stability, solubility, and affinity for ligands. Multiple properties may be screened simultaneously or individually. Proteins may be purified or unpurified, depending on the requirements of the assay. In one embodiment, the screen is a qualitative or quantitative binding assay for binding of conjugates to a protein or nonprotein molecule that is known or thought to bind the conjugate. In another embodiment, the screen is a binding assay for measuring binding to an antibody's target antigen, wherein the antibody is within the conjugate. In an alternate embodiment, the screen is an assay for binding of conjugates to a ligand. Said ligands may be from any organism, with humans, mice, rats, rabbits, and monkeys preferred. Ligands may also encompass surfaces (such as the surface of an ELISA plate), nanoparticles, drugs, etc. Binding assays can be carried out using a variety of methods known in the art, including but not limited to FRET (Fluorescence Resonance Energy Transfer) and BRET (Bioluminescence Resonance Energy Transfer)-based assays, Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. Assays may employ a variety of detection methods including but not limited to chromogenic, fluorescent, luminescent, or isotopic labels.

The biophysical properties of conjugate compositions provided herein, for example stability and solubility, may be screened using a variety of methods known in the art. Protein stability may be determined by measuring the thermodynamic equilibrium between folded and unfolded states. For example, conjugates of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of a conjugate protein may be quantitatively or qualitatively determined using a wide range of methods that are known in the art. Methods which may find use in the present invention for characterizing the biophysical properties of conjugate proteins include gel electrophoresis, chromatography such as size exclusion chromatography and reversed-phase high performance liquid chromatography, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising a conjugate could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the conjugate's stability and solubility.

In one embodiment, Fc ligands include, but are not limited, to proteins Z, A and G.

In one embodiment, the conjugate compositions provided herein may find use in an antibody composition that is monoclonal or polyclonal. The antibodies and Fc fusions of the compositions and methods as provided herein may be agonists, antagonists, neutralizing, inhibitory, or stimulatory. In a preferred embodiment, the antibodies of the compositions and methods as provided herein are used to kill target cells that bear the target antigen, for example cancer cells. In an alternate embodiment, the antibodies of the compositions and methods as provided herein are used to block, antagonize, or agonize the target antigen, for example for antagonizing a cytokine or cytokine receptor. In an another embodiment, the antibodies of the compositions and methods as provided herein are used to block, antagonize, or agonize the target antigen and kill the target cells that bear the target antigen.

In one embodiment, surface plasmon resonance (SPR) binding affinity measurements may be taken. Briefly, antibody fragments are derived from the antibodies of interest. A BIAcore-2000 or BIAcore-3000 real-time kinetic interaction analysis system (Biacore Inc., Piscataway, N.J.) may then be used to determine association and dissociation constants of the antibody fragments in binding interactions with immobilized antigen, according the manufacture's instructions. An equilibrium constant, may then be calculated ($K_D$) as known in the art.

In one embodiment, the term "treatment" in the compositions and methods provided herein refers to therapeutic treatment, as well as prophylactic, or suppressive measures for a disease or disorder. Thus, for example, successful administration of an conjugate provided herein prior to onset of the disease results in treatment of the disease. "Treatment" also encompasses administration of an conjugate protein after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented. In another embodiment, a subject or mammal is successfully "treated" for a EGFR-expressing cancer if, after receiving a therapeutic amount of an modified molecule provided herein, the subject shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues.

In one embodiment, provided herein is a method of inhibiting or suppressing a tumor or a cancer tumor in a subject, comprising the step of administering an effective amount of a conjugate composition provided herein.

In one embodiment, the term "tumor" refers to a swelling or lesion formed by an abnormal growth of cells that can be benign, premalignant or malignant which in the case of the latter it will be defined as cancer. In another embodiment, the term "cancer" and "cancerous" refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer. Furthermore, the conjugates of the compositions and methods as provided herein may be used to treat conditions including but not limited to congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; multiple myeloma; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasisas and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and Natural Killer cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases.

A variety of linkers may find use in the compositions and methods provided herein to generate conjugates or Fc fusions. The term "linker", "linker sequence", "spacer", "tethering sequence" or grammatical equivalents thereof refer to a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-terminus of proteins or protein domains, linkage via disulfide bonds, and linkage via chemical cross-linking reagents. In one aspect of this embodiment, the linker is a peptide bond, generated by recombinant techniques or peptide synthesis. In another embodiment the linker is a cysteine linker. In yet another embodiment it is a multi-cysteine linker. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. In one embodiment, the linker is from about 1 to 30 amino acids in length. In another embodiment, the linker is from about 1 to 15 amino acids in length. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers, glycine-alanine polymers, alanine-serine polymers, and other flexible linkers such as the tether for the shaker potassium channel, and a large variety of other flexible linkers, as will be appreciated by those in the art. Suitable linkers may also be identified by screening databases of known three-dimensional structures for naturally occurring motifs that can bridge the gap between two polypeptide chains. In one embodiment, the linker is not immunogenic when administered in a human subject. Thus linkers may be chosen such that they have low immunogenicity or are thought to have low immunogenicity. Another way of obtaining a suitable linker is by optimizing a simple linker, e.g., (Gly4Ser)n, through random mutagenesis. Alternatively, once a suitable polypeptide linker is defined, additional linker polypeptides can be created to select amino acids that more optimally interact with the domains being linked. Other types of linkers that may be used in the compositions and methods provided herein include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). In another embodiment, chemical linkers may enable chelation of an isotope. For example, Carbon-14-labeled 1-isothiocyanatobenzyl-3-methyldiethylene triaminepentaacetic acid (MX-DTPA) is an exemplary chelating agent for conjugation of radionucleotide to the antibody. The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the components of the conjugates of the compositions and methods provided herein.

Pharmaceutical compositions are contemplated wherein fusion conjugate of the compositions and methods provided herein and one or more therapeutically active agents are formulated. Formulations of the conjugates of the compositions and methods provided herein are prepared for storage by mixing said antibody or Fc fusion having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants or polyethylene glycol (PEG). In another embodiment, the pharmaceutical composition that comprises the conjugate of the compositions and methods provided herein is in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The conjugates disclosed herein may also be formulated as immunoliposomes. A liposome is a small vesicle comprising various types of lipids, phospholipids and/or surfactant that is useful for delivery of a therapeutic agent to a mammal. Liposomes containing the conjugates are prepared by methods known in the art, such as described in Epstein et al., 1985, Proc Nat'l Acad Sci USA, 82:3688; Hwang et al., 1980, Proc Nat'l Acad Sci USA, 77:4030; U.S. Pat. Nos. 4,485,045; 4,544,545; and PCT WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, J National Cancer Inst 81:1484).

The conjugates provided herein may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers (which are injectable microspheres composed of lactic acid-glycolic acid copolymer and leuprolide acetate), and poly-D-(-)-3-hydroxybutyric acid) which is a microsphere-based delivery system composed of the desired bioactive molecule incorporated into a matrix of poly-DL-lactide-co-glycolide (PLG).

The conjugates may also be linked to the surfaces of nanoparticles using the linking methods provided herein. In one embodiment, the nanoparticles can be used for imaging or therapeutic purposes.

Administration of the pharmaceutical composition comprising the conjugates provided herein, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of introduction.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Example 1: Facile Method for the Site-Specific, Covalent Attachment of Full-Length IgG onto Nanoparticles Antibodies, most commonly IgGs, have been widely used as targeting ligands in research and therapeutic applications due to their wide array of targets, high specificity and proven efficacy. Many of these applications require antibodies to be conjugated onto surfaces (e.g. nanoparticles and microplates); however, most conventional bioconjugation techniques exhibit low crosslinking efficiencies, reduced functionality due to non-site-specific labeling and random surface orientation, and/or require protein engineering (e.g. cysteine handles), which can be technically challenging. To overcome these limitations, the inventors of the instant application have recombinantly expressed Protein Z, which binds the Fc region of IgG, with an UV active non-natural amino acid benzoylphenylalanine (BPA) within its binding domain. Upon exposure to long wavelength UV light, the BPA is activated and forms a covalent link between the Protein Z and the bound Fc region of IgG. This technology was combined with expressed protein ligation (EPL), which allowed for the introduction of a fluorophore and click chemistry-compatible azide group onto the C-terminus of Protein Z during the recombinant protein purification step. This enabled crosslinked-Protein Z-IgG complexes to be efficiently and site-specifically attached to aza-dibenzycyclooctyne-modified nanoparticles, via copper-free click chemistry.

Experimental Section

Materials:

An azido fluorescent peptide (AzFP) with the sequence $NH_2$-CDPEK(5-FAM)DSGK($N_3$)S—$CONH_2$ was custom synthesized by Anaspec (Fremont, CA). The K(5-FAM) represents a lysine with a 5-carboxyfluorescein covalently attached to its side chain amino group and the K($N_3$) represents a lysine with an azido group attached to its side chain-amino group. The ADIBO-NHS ester was synthesized as previously described. The SPIO coating material, dextran T10, was purchased from Pharmacosmos (Denmark). Mouse Anti-BSA monoclonal antibody in ascites (B2901) was acquired from Sigma Aldrich (St. Louis, MO), and clinical grade anti-CD20 antibody, rituximab, was obtained from Genentech (South San Francisco, CA). Human lymphoma B cells (Burkitt GA-10) were obtained from the American Type Culture Collection (Manassas, VA). The 70 mm volume coil used for radiofrequency transmission and reception was purchased from Insight Neuroimaging Systems, LLC (Worcester, MA). All other reagents were purchased from Thermo Fisher Scientific (Waltham, MA) unless otherwise noted.

Cloning of Protein Z Recombinant Protein into pTXB1 Vector: Two complimentary oligonucleotides encoding the Protein Z amino acid sequence and flanked at both ends by 15 base sequences homologous to the desired restriction sites of the destination vector were ordered from Integrated DNA Technologies (Coralville, IA). To improve subsequent cleavage from the affinity column, an additional 9 base pairs encoding a "MRM" amino acid sequence were included in the oligonucleotides at the C-terminal end of the Protein Z sequence. The full amino acid sequence for the Protein Z can be found in Supporting Information.

Oligonucleotides were incubated together at a final concentration of 5 µM and hybridized at room temperature for 30 min. The resulting Protein Z sequence was gel purified and directly ligated with gel-purified NdeI-SapI double digested pTXB1 vector (New England Biolabs, Inc) via the CloneEZ kit (Genscript). Insertion of the Protein Z sequence was verified by DNA sequencing using the T7 promoter as the sequencing primer. Site-directed mutagenesis of selected codons into amber codon (TAG) was done using Quikchange Mutagenesis Kit (Agilent).

Expression and Purification of Protein Z Recombinant Protein: The pTXB1 and pEVOL-pBpF (Prof. Peter Schultz, Addgene.org) plasmids were cotransformed into the T7 Expression Crystal Competent Cells (New England Biolabs). Bacterial cell cultures were initially grown overnight in an air shaker (225 rpm) at 37° C. in 3 mL of lysogeny broth (LB) media. Cultures were scaled up to 50 mL of LB media and grown overnight under the same conditions, and then inoculated into 1 L LB media containing 50 mg/L of ampicillin and 25 mg/L of chloramphenicol.

At optical density (OD) 600 nm=0.6, Isopropyl β-D-1-thiogalactopyranoside (IPTG) was added to a final concentration of 0.5 mM to induce T7 RNA polymerase-based expression. For BPA incorporation, L-benzoylphenylalanine (Bachem, King of Prussia, PA) was added into the culture for a final concentration of 300 µM and the culture was left to grow for 30 min. Next, IPTG was added to a final concentration of 0.5 mM and arabinose to a final concentration of 0.1% to begin induction.

Cultures were allowed to express for 2 h at 37° C. Bacterial cultures were centrifugally pelleted at 10,000 g for 5 min, resuspended in 5 mL of column buffer (20 mM Na-HEPES, 0.5 M NaCl, 1 mM EDTA, pH 8.5) containing 0.75 g/L lysozyme and 50 mM phenylmethylsulfonyl fluoride. Cells were lysed by pulse sonication on ice. Cells were centrifuged at 15,000 g for 30 min at 4° C. Supernatant was collected and stored at −20° C. For the following purification steps, all procedures were run at 4° C. The supernatant (1 mL) was incubated for 10 min in a 10 mL Poly-Prep chromatography column (Bio-Rad, Hercules, CA) packed with 1 mL of chitin beads (New England Biolabs, Inc). Supernatant was allowed to pass through the column and chitin beads were washed with 50 mL of column buffer at a flow rate of approximately 2 mL/min.

Expressed Protein Ligation: MESNA (3 mL, 50 mM pH 7.4) was quickly passed through the column in order to evenly distribute the MESNA throughout the chitin beads, and flow was stopped. To make AzFP-ligated Protein Z, the AzFP (0.1 mM) was added into the column and incubated overnight at room temperature. For cysteine-ligated protein Z, free cysteine (0.1 mM) was added instead of AzFP into the column and incubated overnight at room temperature. The next day the column was eluted using 4 mL buffer (0.1 M Tris-HCl, pH 8.5). The EPL product and excess AzFP or cysteines were separated on a Superdex 30 chromatography column Purification and concentration of the final product can also be performed using a 3 kD molecular weight cut-off (MWCO) filter.

16% Tricine-SDS-PAGE gels were used to visualize the separation between the cysteine and AzFP ligated Protein Zs. Gels were run in accordance with previously published methods for the visualization of small proteins.

Protein Z can also be purified further with RP-HPLC (Varian Prostar). A C8 300 µm 5 µm column (Varian) was used. Protein Zs were eluted at 1 mL/min using a mixture of water and acetonitrile, both containing 0.1% TFA. The solvent gradient used was: 95%-75% water over the first 10 min, then 75%-69% over the next 60 min. Absorbance was monitored at 215 nm. The collected fractions were then dried using vacuum centrifuge concentrator (Labconco) and reconstituted in 0.1 M Tris-HCl buffer, pH 8.5.

Photocrosslinking: Stock rituximab (10 mg/mL) was diluted to 1 mg/mL in 0.1 M Tris buffer and mixed with HPLC purified Protein Z at the final concentrations of 100 µg/mL rixtuximab and 1 mg/mL Protein Z or Protein Z-AzFP. Incubation was done at 25° C. for 1 hour with shaking. Afterwards, the sample was then placed in an ice bath under a 365 nm UV lamp (UVP UV L56, Upland, CA) for 3 hours.

Uncrosslinked Protein Z was then dissociated by buffer exchanging with pH 3.5 buffer (0.2 M Glycine). Both dissociated and excess Protein Z were then filtered out using an Amicon 50 kDa MWCO filter. The buffer was then exchanged back to 0.1 M Tris-HCl, pH 8.5 using the filter.

In the case of anti-BSA monoclonal antibody, the ascites fluid was incubated with HPLC-purified Protein Z-AzFP (1 mg/mL) at the volume-to-volume ratio of 1:10, and then UV crosslinked as above. The crosslinked solution was then washed 3 times using 0.2 M Glycine buffer and filtered with a 50 kDa MWCO filter as above and finally buffer exchanged back into 0.1 M Tris-HCl, pH 8.5 for a final dilution of 1:10 of the original ascites.

SPIO Nanoparticle Synthesis and Amination: Dextran-coated SPIO nanoparticles (NPs) were prepared using the co-precipitation method. Specifically, 1.5 g $FeCl_2$ and 4 g $FeCl_3$ were each dissolved in 12.5 mL of degassed $dH_2O$ and added to 25 g dextran T10 in 50 mL $diH_2O$. Keeping this mixing solution at 4° C., 15 mL ammonium hydroxide was slowly added to this mixture. The resulting black solution was then heated to 90° C. for 1 h and cooled overnight. Purification of SPIO NPs was accomplished by ultracentrifugation of the mixture at 20 k relative centrifugal force (RCF) for 30 min Pellets were discarded, and the supernatant was subjected to diafiltration against greater than 20 volumes of 0.02 M citrate, 0.15 M sodium chloride buffer using a 100 kDa MWCO filter (GE Healthcare). The purified particles were then crosslinked by reacting the particles (10 mg Fe $mL^{-1}$) with 25% (v/v) 10 M NaOH and 33% epichlorohydrin. After mixing for 24 h, the particles were briefly dialyzed and then functionalized with amines by adding 25% ammonium hydroxide. This reaction was allowed to continue for another 24 h followed by diafiltration as described above.

ADIBO Modification of SPIO Nanoparticles: Surface amines on dextran-coated SPIO NPs (5 mg/mL) were reacted with the amine-reactive ADIBO-NHS, diluted 10 times from stock (138 mM) in dimethyl sulfoxide (DMSO), in 0.1 M sodium phosphate buffer, pH 9. The linker was added at 100 times molar excess to the aminated SPIO nanoparticles. All nanoparticles solutions were mixed overnight at room temperature. ADIBO-SPIO NPs were purified via PD-10 chromatography columns (GE Healthcare, Piscataway, NJ).

Copper-free click conjugation of ADIBO-SPIO NPs was performed by mixing the SPIO NP (2 mg/mL) with 30 µM of filtered Pz-rituximab in sodium carbonate buffer (pH 8). Reactions were mixed overnight at room temperature and then purified on MACS µcolumns (Miltenyi Biotec, Bergisch Gladbach, Germany) and equilibrated with PBS.

Dynamic light scattering (DLS) measurements were performed on a Zetasizer Nano from Malvern Instruments. (Malvern Instruments, Malvern, UK) The scattering angle was held constant at 90°.

Microscopy and Flow Cytometric Analysis: SPIO NPs were incubated with 100 µL of $4 \times 10^6$ cells/mL Burkitt GA-10 lymphoma B cells for 30 minutes at 37° C., 5% $CO_2$, in a 96-well plate. SPIO NPs were added at final concentrations of 10 µg Fe/mL. In the antibody inhibition experiments, 100 µg/mL (final concentrations) of free anti-CD20 was added prior to the addition of the antibody-conjugated NPs. The free, unbound particles were purified from the cells through three PBS washes at 1,000 RCF for 5 minutes each. Cells were finally resuspended in 300 µL of PBS and placed in a 96-well plate.

Microscopy images were acquired with an Olympus IX 81 inverted fluorescence microscope using a LUC PLAN 40× objective (numerical aperture 0.6; Olympus) and an SOLA light engine excitation source (Lumencor, Beaverton, OR). Fluorescent images were acquired using a back-illuminated electron multiplying charge-coupled device camera (Andor Technology PLC, Belfast, Northern Ireland).

Flow cytometry of the washed cell samples was performed using a Guava Easycyte Plus system (Guava Technologies, Hayward, CA). Flow cytometry data were analyzed using FlowJo (TreeStar Inc., San Francisco, CA).

Cell Pellet MR Imaging: GA-10 cells were combined to form a single cell pellet for each nanoparticle formulation. The samples were transferred to a 384-well plate, and the cells were pelleted to the bottom of each well with brief, low-speed centrifugation. The plate was then imaged on a 9.4 T magnet interfaced to a Varian INOVA console using a 70 mm inner diameter volume coil for radio-frequency transmission and reception. $T_2^*$-weighted gradient echo (GEMS) MR images were collected using parameters as follows: repetition time (TR)=200 ms, echo time (TE)=5 ms, flip angle=20°, slice thickness=0.5 mm, field of view (FOV) =4 cm×4 cm, number of acquisitions=8, resolution=256× 256.

Results
In Vivo Incorporation of BPA During Protein Expression

The coding sequence for wild-type Protein Z was cloned into an EPL-compatible plasmid pTXB1 (New England Biolabs), generating a construct that encodes Protein Z fused to a self-cleaving intein domain followed by a Chitin Binding Domain (CBD) (FIG. 1A: Ligation). To allow for incorporation of the unnatural amino acid, BPA, into the fusion protein during translation, site-directed mutagenesis was performed to introduce an amber codon (i.e. UAG) into the IgG binding site of Protein Z. The BPA replaced a phenylalanine in the thirteenth position (F13). This site was selected due to the structural similarities between BPA and phenylalanine (BPA is a derivative of phenylalanine), F13's postulated role in IgG binding and the outward orientation of its side chain, which can minimize the possibility of intramolecular crosslinking. Additionally, in order to compare the performance of F13BPA Protein Z with that of the F5BPA variant previously synthesized by others, a second construct was prepared with phenylalanine at the fifth position mutated to BPA.

Figure 2:
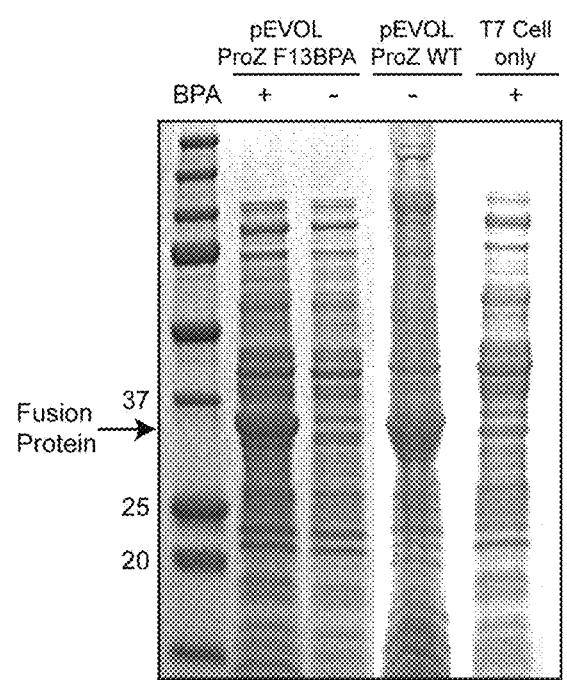
FIG. 2. SDS-PAGE confirming the in vivo incorporation of BPA into expressed Protein Z. T7 competent *E. coli* were co-transformed with the pEVOL-pBpf plasmid containing the amber suppressor tRNA/aminoacyl transferase pair and the pTXB1 plasmid, which codes for Protein Z with an amber codon mutation (ProZ F13BPA). Following induction of protein expression, cell lysates, with or without BPA in the media, were evaluated by SDS-PAGE (lanes 1 and 2, respectively). Analogous studies were performed with *E. coli* that express wild-type Protein Z (lane 3) and unmodified T7 competent cells (lane 4).

Host E. Coli were co-transformed with the pTXB1 plasmids encoding either the photoreactive protein Z or wild-type protein Z and the pEVOL-pBpF plasmid, which carries the tRNA/aminoacyl transferase pair. While the wild type fusion protein could be expressed in the absence of BPA, the amber mutant protein required BPA for expression (FIG. 2). This is expected since, in the absence of BPA, the amber stop codon is not suppressed and translation is terminated early. This also confirms that there is no "leaky" background incorporation of other amino acids in response to the amber codon, as was seen when some other proteins containing UAAs (i.e. ochre codons) were expressed using similar approaches. Additionally, the expression levels for the BPA-containing mutant fusion proteins (F13BPA and F5BPA) were comparable to that of the wild type Protein Z. Representative protein expression data of the F13BPA mutant fusion protein is shown in FIG. 2.

The results on additional BPA-containing mutant fusion proteins including Q32BPA, K35BPA, N28BPA, N23BPA, and L17BPA are discussed below.

Protein Purification and Expressed Protein Ligation

Following protein expression, a ten amino acid peptide (AzFP) with a fluorophore (5-FAM) and an azide moiety was ligated onto the C-terminus of Protein Z via intein-mediated Expressed Protein Ligation (EPL). This enables the crosslinked Protein Z-IgG complexes to be subsequently visualized and attached to alkyne-functionalized substrates via click chemistry. EPL is a versatile technique that allows multiple functional groups to be introduced simultaneously during standard recombinant protein purification procedures, without requiring any additional steps (FIG. 1A, Ligation). The chitin column-bound fusion protein is simply incubated with sodium 2-sulfanylethanesulfonate (MESNA) along with AzFP, causing its ligation to the C-terminus of the Protein Z. Analogous procedures were also performed with cysteine in place of AzFP to create a Protein Z-cysteine ligation product, which was used as an unmodified size standard, while the AzFP-ligated Protein Z (abbrev. Pz-AzFP) was used for conjugation with alkyne-functionalized substrates.

Figure 3:
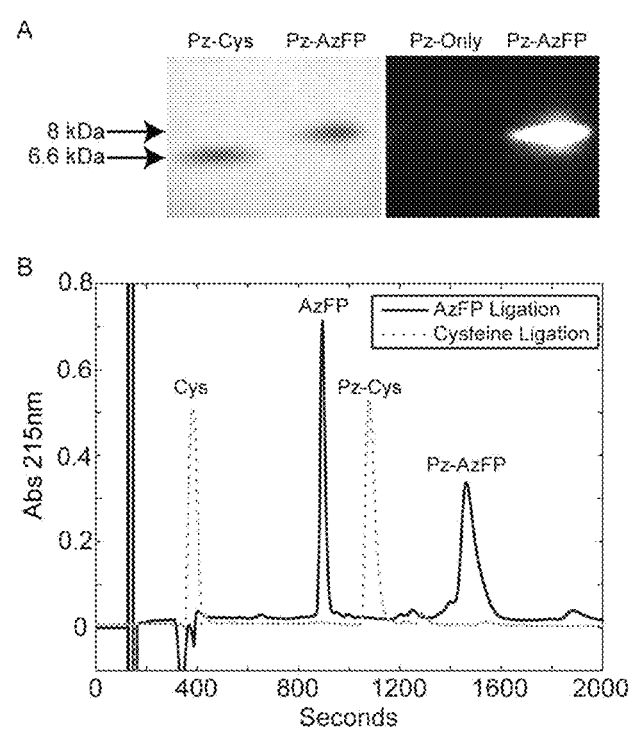
FIG. 3. SDS-PAGE and HPLC analysis of Protein Z following ligation with cysteine or an azido fluorescent peptide. (A) Tricine SDS-PAGE analysis of Protein Z following intein-mediated expressed protein ligation with either a cysteine (Pz-Cys) or an azido-fluorescent peptide (Pz-AzFP). Formation of the conjugate was evaluated via a white light image of the gel (left) and further confirmed by fluorescent imaging of the gel (right), which showed that only the Protein Z-AzFP conjugate was fluorescent. (B) Pz-Cys and Pz-AzFP ligation products were also analyzed by HPLC.

Both the AzFP and cysteine forms of Protein Z were analyzed on a tris-tricine SDS-PAGE gel. Protein bands were visualized by Coomassie-staining and fluorescence (FIG. 3A). The lane containing the AzFP-ligated Protein Z clearly showed a band migrating at the approximate molecular weight of 8 kD, by both Coomassie staining and fluorescence (FIG. 3A, right lane). In contrast, the cysteine-ligated Protein Z was only observed by Coomassie staining, at the expected approximate molecular weight of 6.6 kD, but not by fluorescence (FIG. 3A, left lane).

The two Protein Z variants were further analyzed using reverse-phase HPLC (RP-HPLC). The resulting spectra clearly showed the two variants to be distinct species, with the Protein Z-AzFP variant eluting in more organic conditions due to the addition of the AzFP peptide (FIG. 3B).

UV-Induced Protein Z Crosslinking onto IgG

Figure 4:
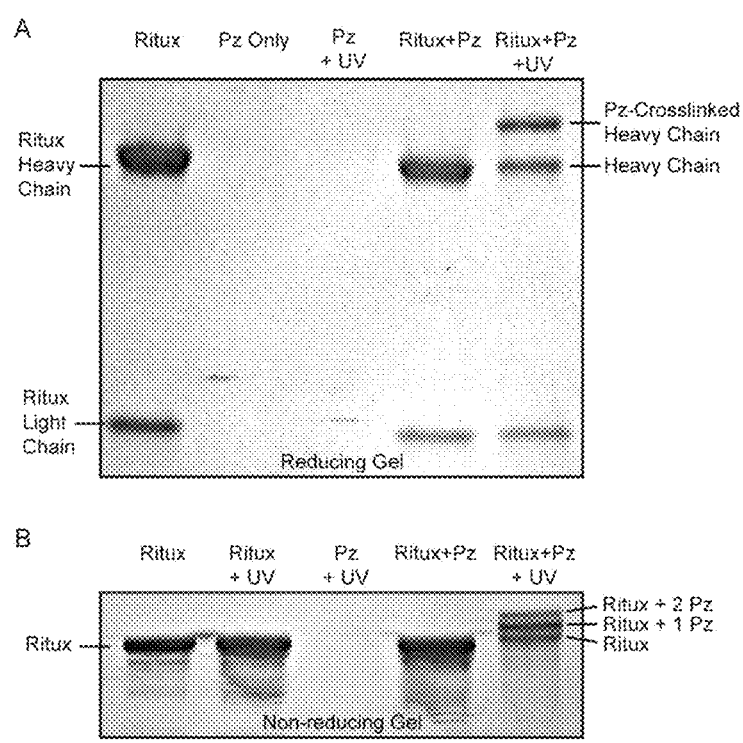
FIG. 4. Evaluation of UV crosslinked Protein Z-rituximab conjugates via SDS-PAGE. Samples containing photoreactive Protein Z and/or rituximab (Ritux) were UV or mock irradiated and analyzed via SDS-PAGE under reducing and non-reducing conditions. (A) The reducing gel shows that the exposure of samples containing photoreactive Protein Z and rituximab to UV irradiation results in an additional band above the heavy chain (lane 5), corresponding to Protein Z crosslinked heavy chains. No additional bands were observed above the light chain. (B) The non-reducing gel clearly shows the appearance of two additional bands when rituximab is crosslinked with Protein Z (lane 5), corresponding to 1 or 2 crosslinked Protein Z per IgG. The formation of the additional bands is dependent on both the presence of rituximab and Protein Z, as well as on exposure to UV.

To crosslink photoreactive Protein Z onto IgGs, the F13BPA variant was first incubated with the humanized IgG1 monoclonal antibody rituximab and exposed to long wavelength UV light (365 nm) (FIG. 1B: Crosslinking). The extent of crosslinking was assessed using both reducing and non-reducing SDS-PAGE gels. In the reducing gel, the formation of an additional band above the IgG heavy chain was clearly observed after the crosslinking procedure (FIG. 4A). This additional band corresponds to those IgG heavy chains that have been crosslinked with a Protein Z. No analogous band was observed above the IgG light chain, indicating the Fc-specific nature of Protein Z binding and crosslinking.

While the reducing SDS-PAGE showed that approximately 50% of the heavy chains were crosslinked, which would be consistent with one Protein Z per IgG, it has previously been reported that each IgG could bind up to two Protein Zs. Therefore analysis was also performed using a non-reducing SDS-PAGE gel, which did in fact show two additional bands in the crosslinked rituximab sample, corresponding to whole rituximab crosslinked with either one or two Protein Zs (FIG. 4B). Image analysis of the gel showed that up to 80% of rituximab was crosslinked with at least one Protein Z.

Figure 5:
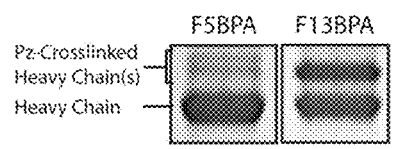
FIG. 5. Comparison of IgG crosslinking using FSBPA and F13BPA variants of Protein Z. Rituximab was incubated with the FSBPA or F13BPA variants of Protein Z and exposed to UV irradiation. Protein Z-IgG conjugates were evaluated via a reducing SDS-PAGE gel. The amino acid sequence of the photoreactive protein Z is: VDNKFNKEQQNAFYEILHLPNLNEEQRNAFIQS LKDDPS QS ANLLAEAKKLNDAQAP KMRM (SEQ ID NO: 1). The amino acids that were mutated to BPA are shown is underlined.

In addition to the F13BPA variant, the F5BPA variant of Protein Z, as previously reported by Konrod et al., was also crosslinked onto rituximab under the same conditions. Compared to the F13BPA variant, which showed 50% crosslinking as assessed by reducing gel, the F5 variant showed a significantly lower crosslinking efficiency of only 20% (FIG. 5). Additionally, the F5BPA variant was observed to form two additional bands upon crosslinking. It is speculated that the BPA may be forming crosslinks to two different sites within the IgG heavy chain, thereby generating differentially unfolded proteins with different migration shifts.

Figure 10:
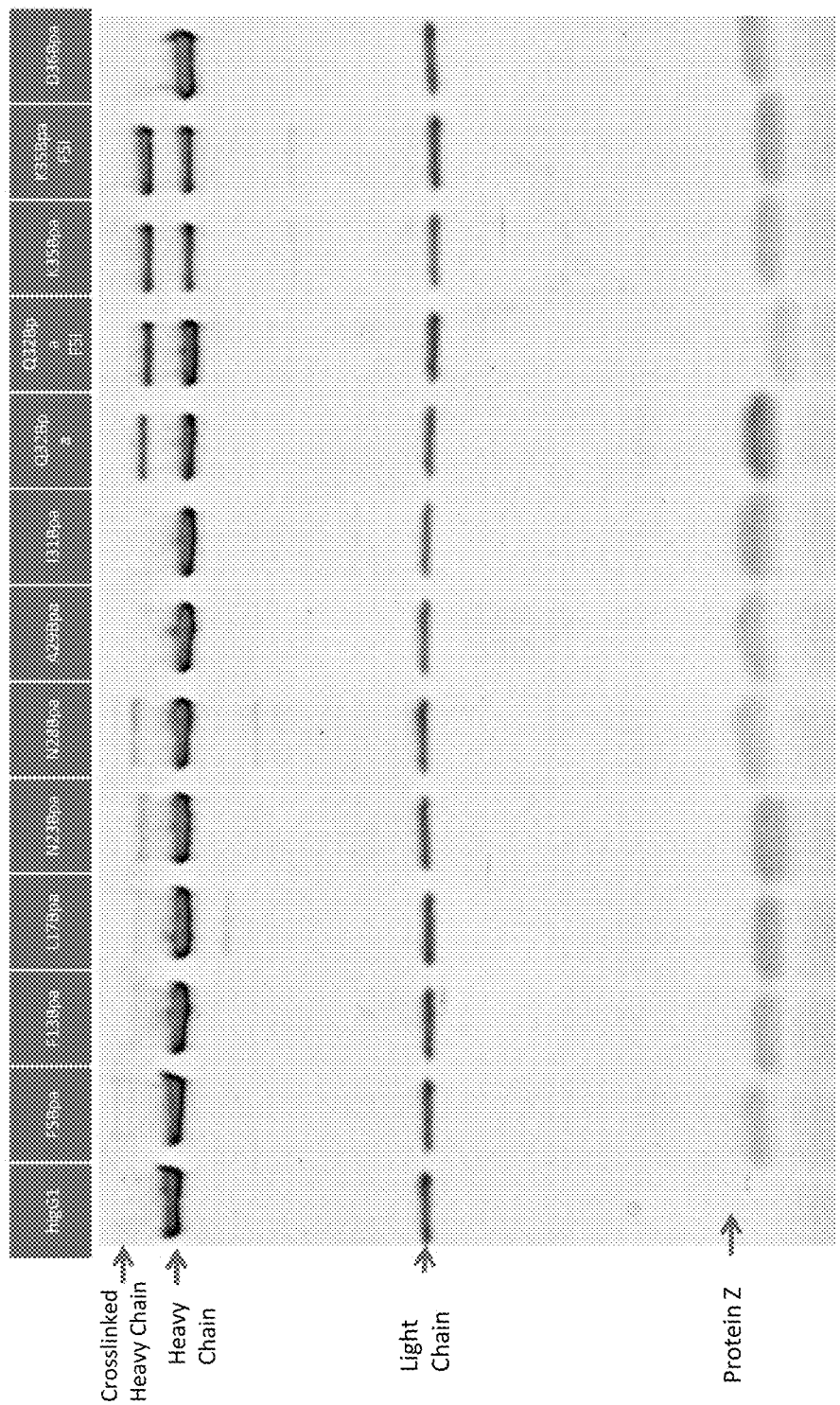
FIG. 10 shows that hIgG1 crosslinks significantly with Q32Bpa and K35Bpa.

Results were obtained for additional BPA-containing mutant fusion proteins including Q32BPA, K35BPA, N28BPA, N23BPA, and L17BPA. As shown in FIG. 10, hIgG1 crosslinks significantly with Q32Bpa & K35Bpa. Humanized IgG1 (hIgG1) antibody (rituximab) was crosslinked under 350 nm UV light for one hour with Protein Zs containing a Bpa placed at various sites in the protein as indicated. Additionally, Protein Zs with a FM mutation combined with either Q32Bpa or K35Bpa mutations were also used. The reactions were then run on a reducing SDS-PAGE gel and stained for proteins using Coomassie stain. It was found that K35Bpa variants can best crosslinked human IgG1, followed by Q32Bpa. The crosslinking extents with these variants are significantly better than those of the previously reported F5Bpa or F13Bpa variants. The addition of F5I mutation did seem to alter crosslinking.

Figure 11:
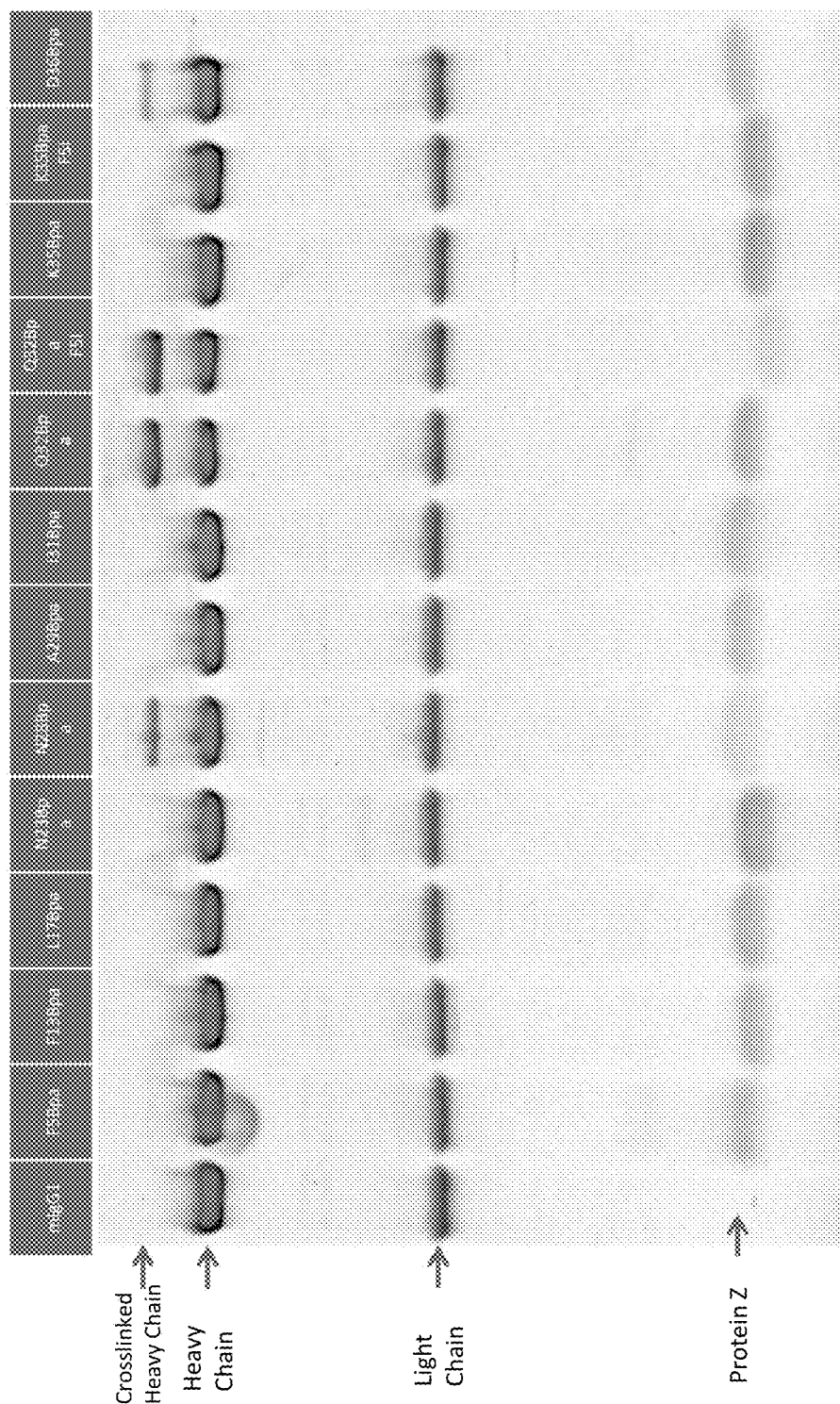
FIG. 11 shows that mIgG1 crosslinks significantly with Q32Bpa, N28Bpa and K35Bpa.

As shown in FIG. 11, mIgG1 crosslinks significantly with Q32Bpa, N28Bpa and K35Bpa. A mouse IgG1 (mIgG1) antibody (anti-Cy5) was crosslinked under 350 nm UV light for one hour with Protein Zs containing a Bpa placed at various sites in the protein as indicated. The reactions were then run on a reducing SDS-PAGE gel and stained for proteins using Coomassie stain. Wildtype Protein A or Protein Z are not known to bind to mIgG1. While neither the F5Bpa nor F13Bpa showed any appreciable crosslinking, N28Bpa, Q32Bpa and D36Bpa variants were shown to be able to best cross-linked the mIgG1 subtype. The addition of FM mutation did seem to alter crosslinking.

Figure 12:
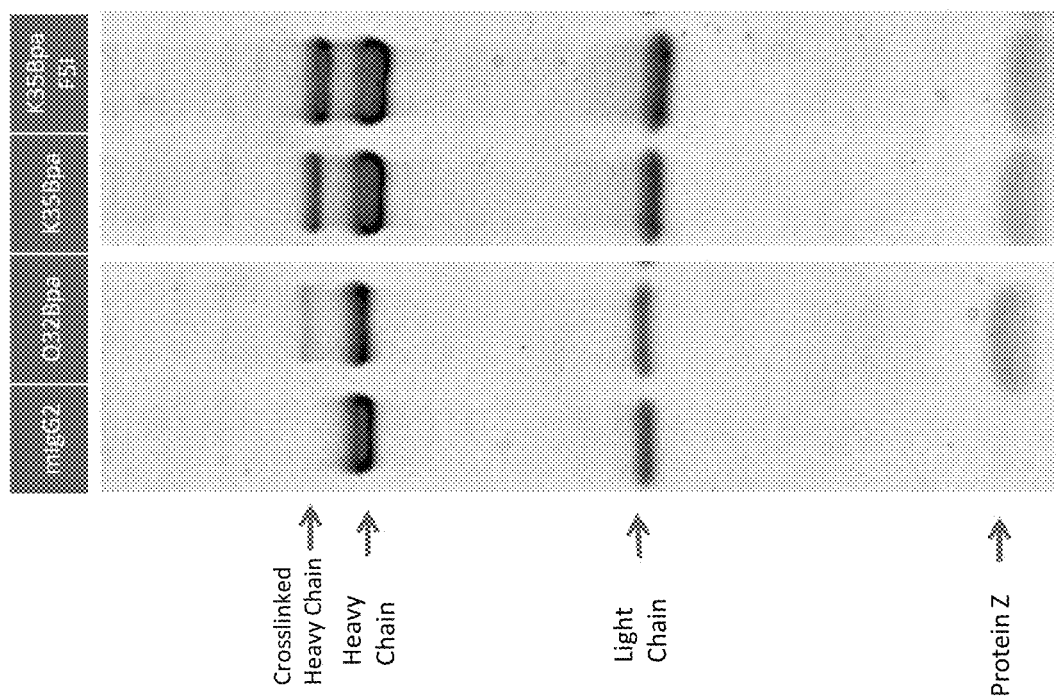
FIG. 12 shows that mIgG2 crosslinks significantly with K35Bpa.

FIG. 12 shows that mIgG2 crosslinks significantly with K35Bpa. A mouse IgG2 (mIgG2) antibody (OKT3) was crosslinked under 350 nm UV light for one hour with Protein Zs containing a Bpa placed at various sites in the protein as indicated. The reactions were then run on a reducing SDS-PAGE gel and stained for proteins using Coomassie stain. While Q32Bpa showed some crosslinking, K35Bpa and K35Bpa FM variants of Protein Z showed the best crosslinking performances. The addition of FM mutation slightly improves crosslinking efficiency.

Figure 13:
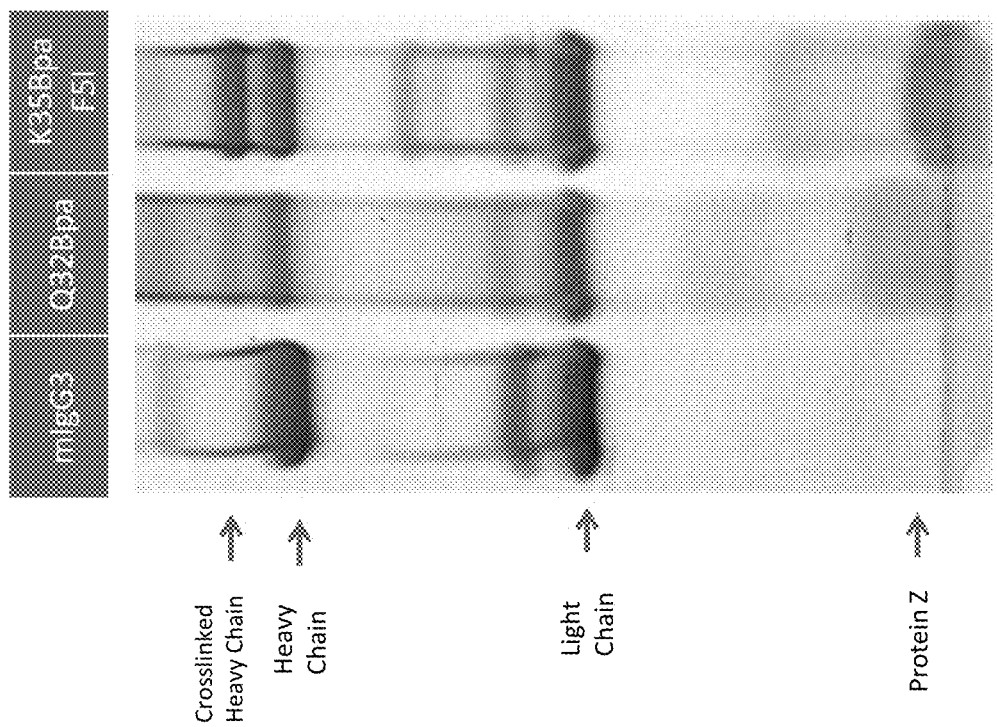
FIG. 13 shows that mIgG3 crosslinks significantly with K35Bpa.

FIG. 13 shows that mIgG3 crosslinks significantly with K35Bpa. A mouse IgG3 (mIgG3) antibody was crosslinked under 350 nm UV light for one hour with Protein Zs containing a Bpa placed at various sites in the protein as indicated. The reactions were then run on a reducing SDS-PAGE gel and stained for proteins using Coomassie stain. While Q32Bpa showed some crosslinking, K35Bpa FM variant of Protein Z again showed the best crosslinking performance.

Figure 14:
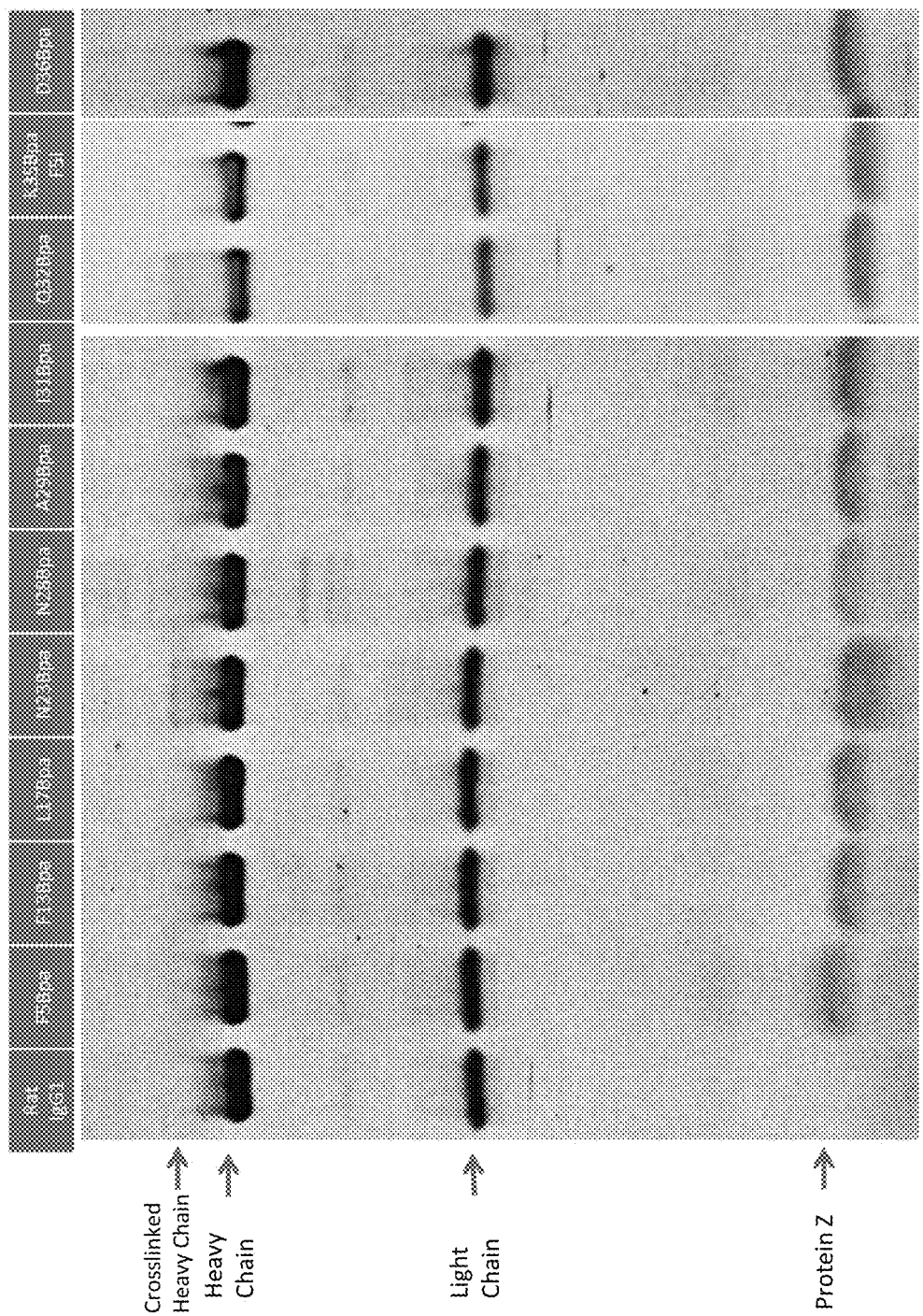
FIG. 14 shows that Rat IgG1 Crosslinks with N23Bpa.

As shown in FIG. 14, Rat IgG1 crosslinks with N23Bpa. A rat IgG1 antibody was crosslinked under 350 nm UV light for one hour with Protein Zs containing a Bpa placed at various sites in the protein as indicated. The reactions were then run on a reducing SDS-PAGE gel and stained for proteins using Coomassie stain. While wildtype Protein A or Protein Z are not known to bind rat IgG1, N23Bpa and Q32Bpa variants of Protein Z displayed the ability to crosslink rat IgG1.

Figure 15:
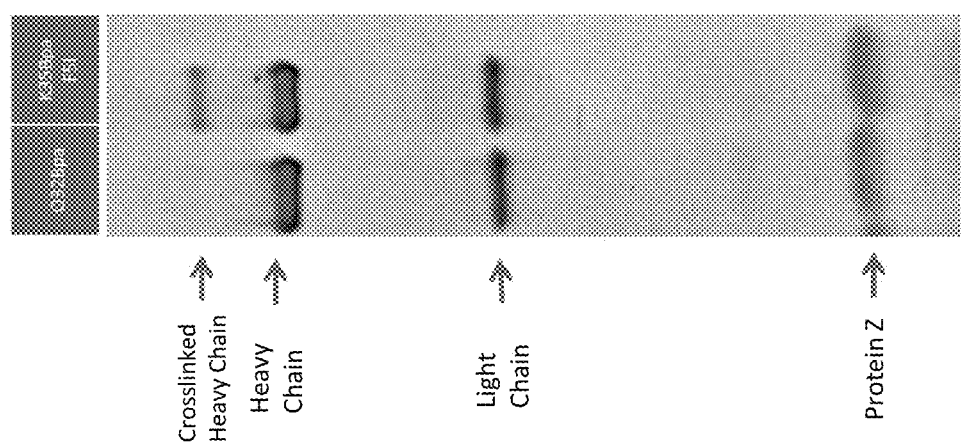
FIG. 15 shows that Rat IgG2a crosslinks significantly with K35Bpa.

As shown in FIG. 15, Rat IgG2a crosslinks significantly with K35Bpa. A rat IgG2a antibody was crosslinked under 350 nm UV light for one hour with Protein Zs containing a Bpa placed at various sites in the protein as indicated. The reactions were then run on a reducing SDS-PAGE gel and stained for proteins using Coomassie stain. While wildtype Protein A or Protein Z are not known to bind rat IgG2a, K35Bpa F5I variants of Protein Z displayed the ability to significantly crosslink rat IgG2a.

Figure 16:
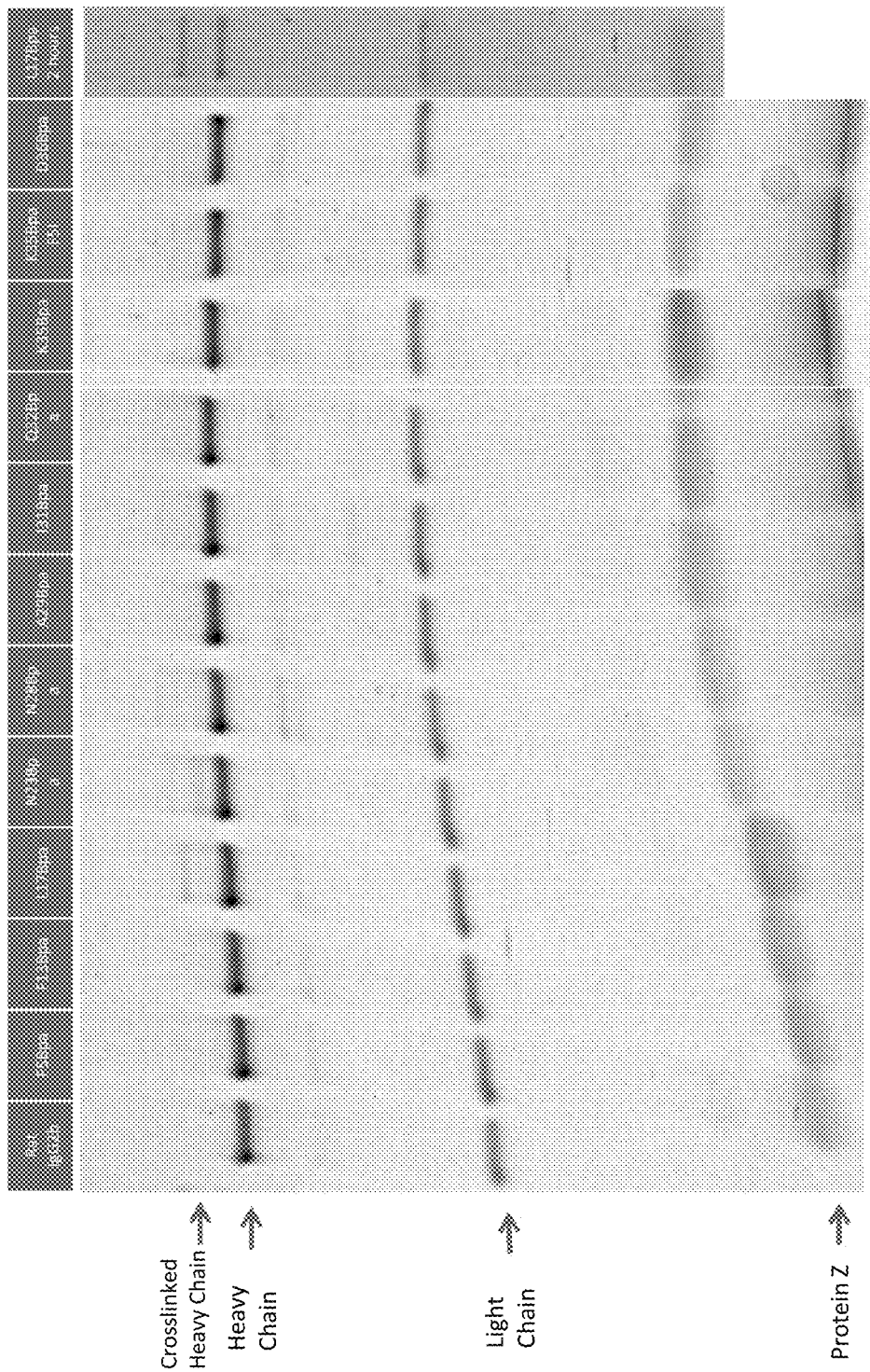
FIG. 16 shows that Rat IgG2b crosslinks significantly with L17Bpa.

FIG. 16 shows that Rat IgG2b crosslinks significantly with L17Bpa. A rat IgG2b (YN-1) antibody was crosslinked under 350 nm UV light for one hour with Protein Zs containing a Bpa placed at various sites in the protein as indicated. The reactions were then run on a reducing SDS-PAGE gel and stained for proteins using Coomassie stain. While wildtype Protein A or Protein Z are not known to bind rat IgG2b, L17Bpa variants of Protein Z displayed the ability to crosslink rat IgG2b. When UV exposure is extended to 3 hours, significant extent of antibody crosslinking is observed with L17Bpa.

Figure 17:
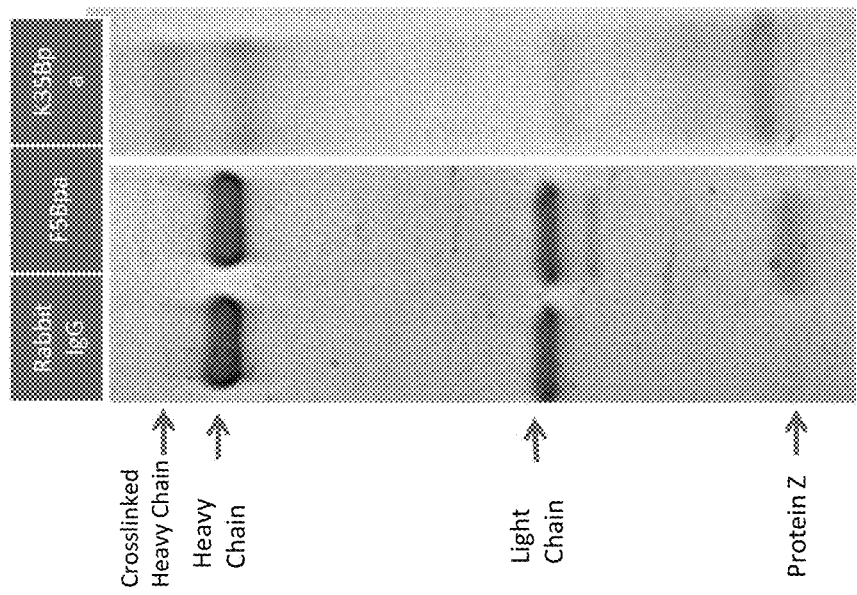
FIG. 17 shows that Rabbit IgG crosslinks significantly with K35Bpa.

FIG. 17 shows that Rabbit IgG crosslinks significantly with K35Bpa. A rabbit polyclonal antibody was crosslinked under 350 nm UV light for one hour with Protein Zs containing a Bpa placed at various sites in the protein as indicated. The reactions were then run on a reducing SDS-PAGE gel and stained for proteins using Coomassie stain. While F5Bpa displayed little crosslinking, K35Bpa variants of Protein Z displayed the ability to appreciably crosslink rabbit polyclonal antibody.

Figure 18:
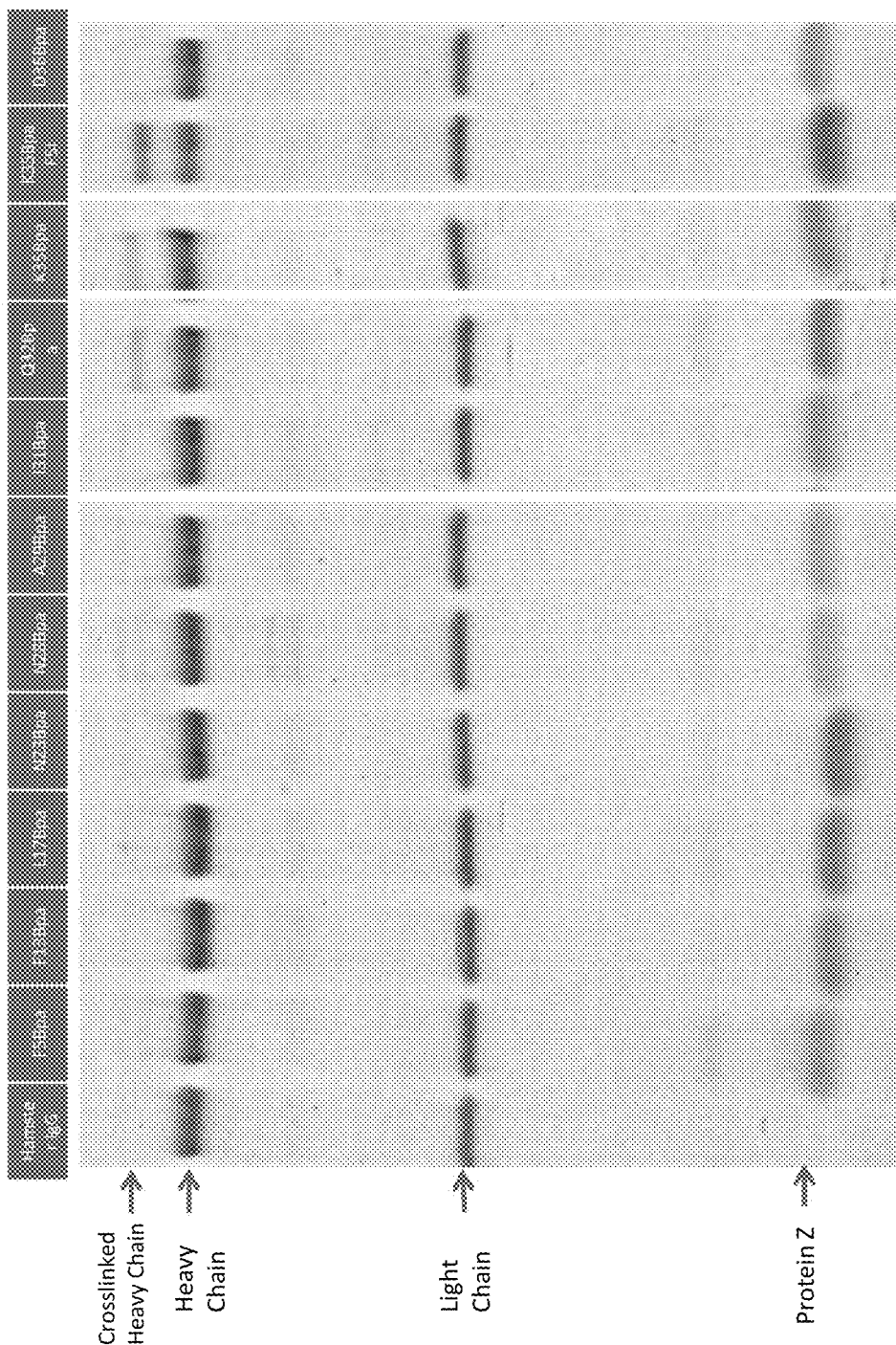
FIG. 18 shows that Hamster IgG1 crosslinks significantly with Q32Bpa and K35Bpa.

FIG. 18 shows that Hamster IgG1 crosslinks significantly with Q32Bpa and K35Bpa. A hamster IgG1 (145-2C11) antibody was crosslinked under 350 nm UV light for one hour with Protein Zs containing a Bpa placed at various sites in the protein as indicated. The reactions were then run on a reducing SDS-PAGE gel and stained for proteins using Coomassie stain. Appreciable crosslinking was achieved with Q32Bpa, K35Bpa and K35Bpa F5I variants of Protein Z. The addition of F5I mutation to K35Bpa enhanced the ability to crosslink hamster IgG1.

Figure 19:
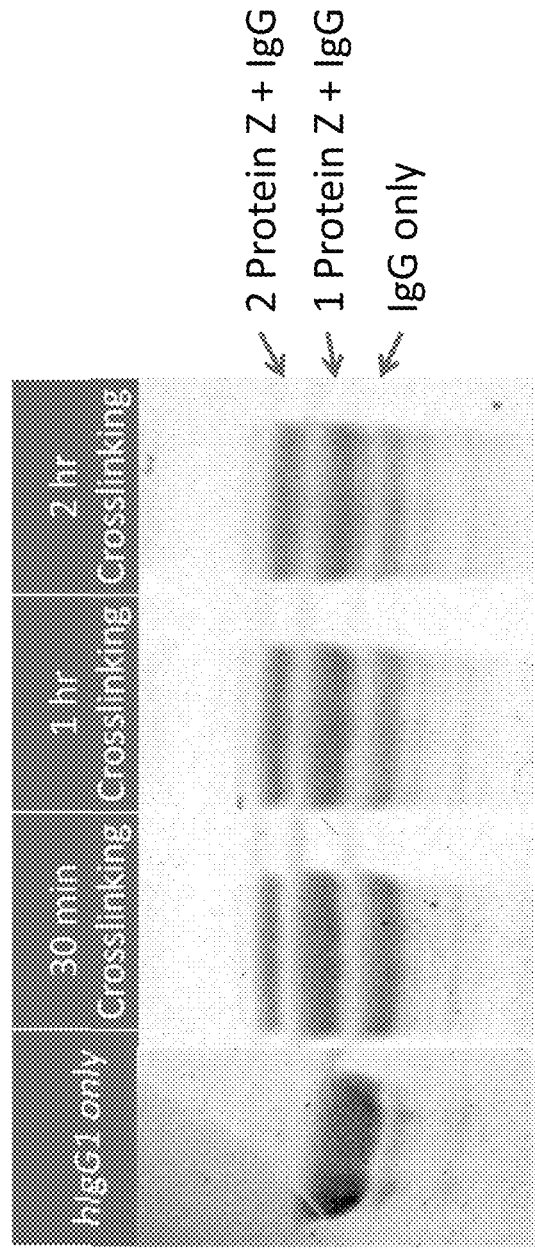
FIG. 19 shows fast Crosslinking with K35Bpa Variant.

FIG. 19 shows fast crosslinking with K35Bpa Variant. K35Bpa variant of Protein Z was crosslinked with 350 nm UV for various lengths of time with the same amount of human IgG1 (rituximab) The reactions were then run on a non-reducing SDS-PAGE gel and stained for proteins using Coomassie stain. The gel shows that significant amount of crosslinking (75%) was achieved within the first one hour.

Compared to previously reported F5Bpa mutation, K35Bpa shows much faster crosslinking kinetics.

As shown in FIG. 20, no pre-incubation is needed for crosslinking with K35BPA of Protein Z. K35Bpa variant of Protein Z was crosslinked with human IgG (rituximab) with or without pre-UV incubation. The reactions were then run on a reducing SDS-PAGE gel and stained for proteins using Coomassie stain. The results show that no pre-incubation is needed, this means crosslinking can be done by directly applying UV after mixing Protein Z and IgG.

Figure 21A:
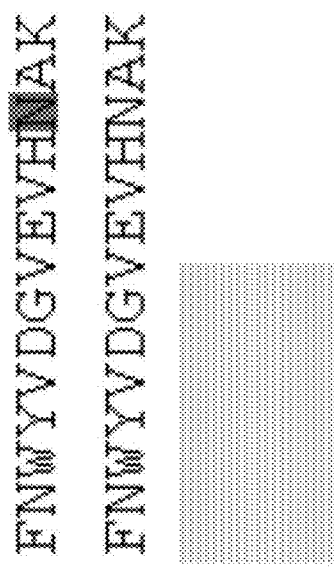
FIGS. 21A and 21B show LC-MS indicating the location of the covalent crosslinking.
Figure 21B:
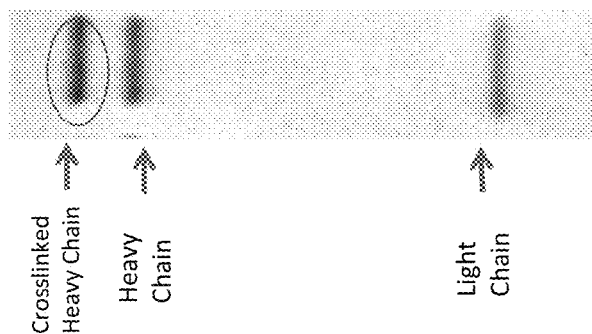

As shown in FIGS. 21A and B, LC-MS shows the location of the covalent crosslinking. LC-MS analysis of the hIgG1 heavy chain crosslinked with Protein Z (circled band in SDS-PAGE gel) shows that Protein Z crosslinks onto Leucine 409 on the IgG heavy chain (above). The circled band was cut out of the gel, digested with trypsin, and analyzed by LC-MS/MS on an LTQ-Orbitrap XL mass spectrometer. MS/MS spectra generated from the mass spec were searched against a custom *E. coli*/Sf9 database using SEQUEST. Full tryptic specificity was used for SEQUEST search.

Figure 22B:
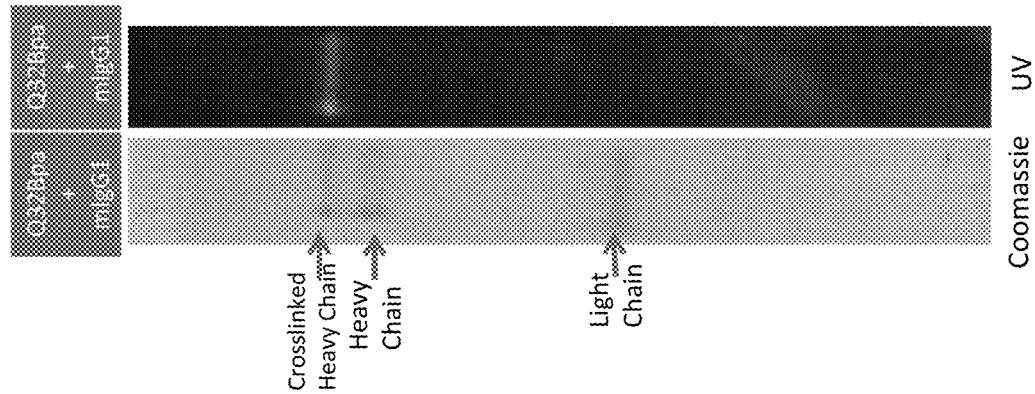
FIGS. 22A and 22B show azide-FITC modified protein Z for Fc region site-specific conjugation of IgG.
Figure 22A:
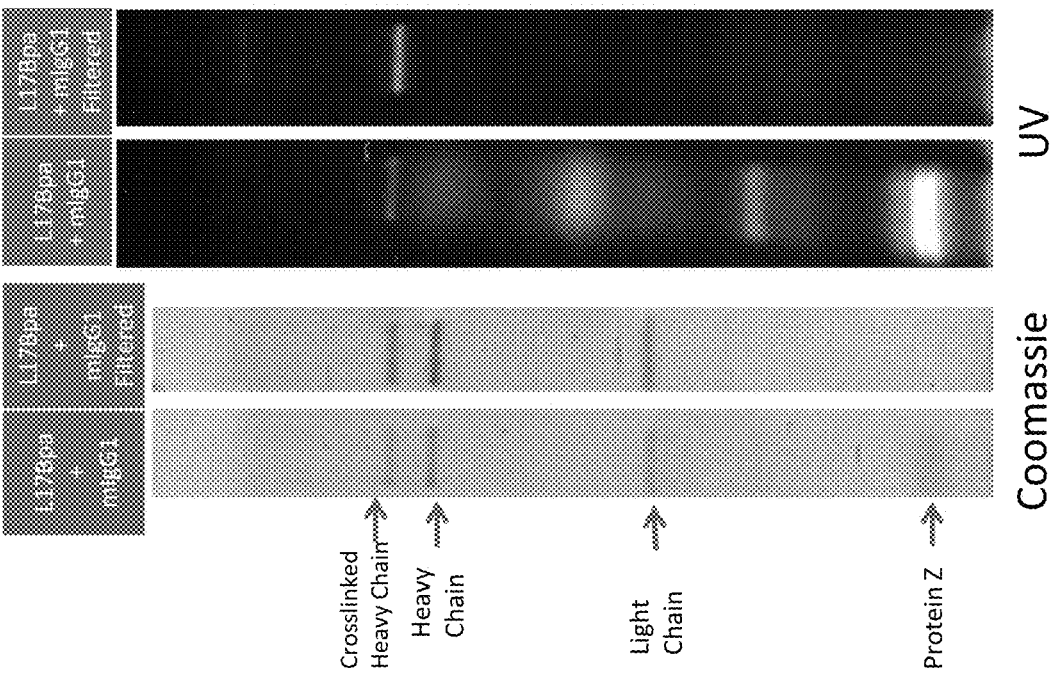

FIGS. 22A and B show azide-FITC modified protein Z for Fc region site-specific conjugation of IgG. L17Bpa variant of Protein Z was EPL ligated to a peptide containing azide and FITC during the purification process. The resulting Protein Z was then crosslinked with rat IgG2b (YN-1) for 2 hour under 350 nm UV light. Excess and non-crosslinked Protein Z were filtered out using a 50 KD cutoff filter column. The resulting reactions were run on a reducing SDS-PAGE gel and imaged for fluorescence (UV) and protein (Coomassie). Significant crosslinking was observed and no free Protein Z was seen after filtering. Q32Bpa variant of Protein Z was EPL ligated to a peptide containing azide and FITC during the purification process. The resulting Protein Z was then crosslinked with mouse IgG1 for 2 hour under 350 nm UV light. Excess and non-crosslinked Protein Z were filtered out using a 50 KD cutoff filter column. The filtered product was run on a reducing SDS-PAGE gel and imaged for fluorescence (UV) and protein (Coomassie). Significant crosslinking was observed and no free Protein Z was seen after filtering.

Figure 23:
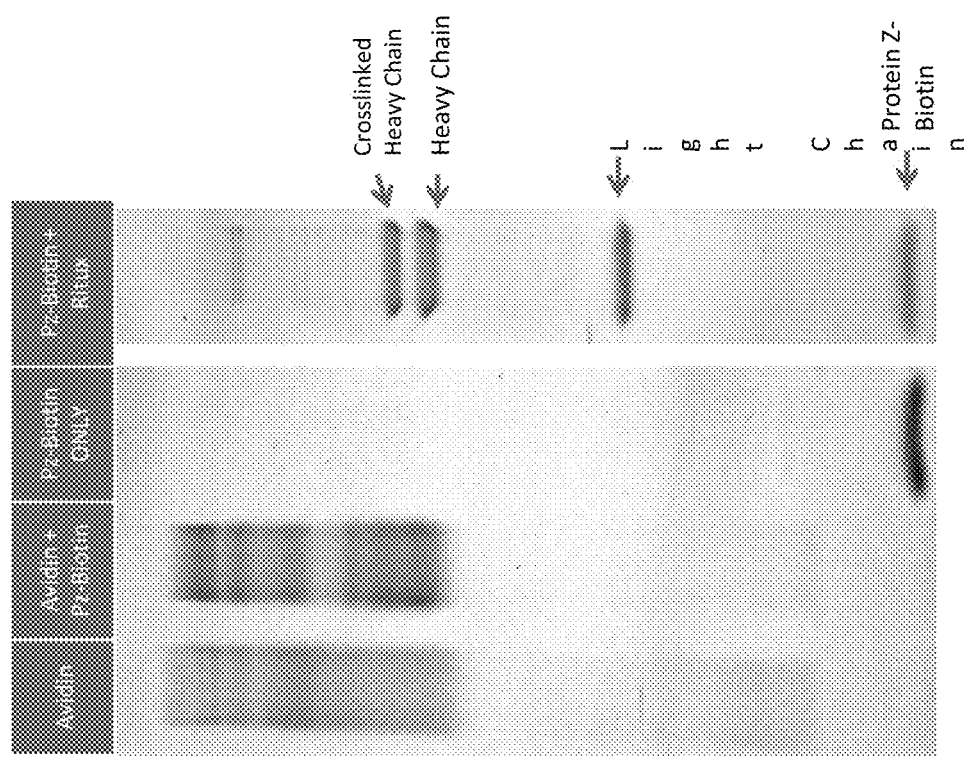
FIG. 23 shows biotin modified protein Z for Fc region site-specific IgG biotinylation.

FIG. 23 shows biotin modified protein Z for Fc region site-specific IgG biotinylation. The modularity feature of EPL fusion protein allows many different modifications of Protein Z. In particular, the addition of a biotin is attractive due to biotinylated antibodies' broad downstream applications. Here, K35bpa Protein Z was EPL ligated to a biotin-containing peptide during the purification process. The resulting Protein Z was then crosslinked with hIgG1 (rituximab) for 1 hour under 350 nm UV light. The Coomassie stained SDS-PAGE gel shows the Protein Z to contain a biotin moiety as demonstrated by the shift in Protein Z migration when it is mixed with avidin (Lane 1-3, no boiling). The biotinylated Protein Z was shown to able to crosslink human IgG1 (Lane 4).

Figure 24:
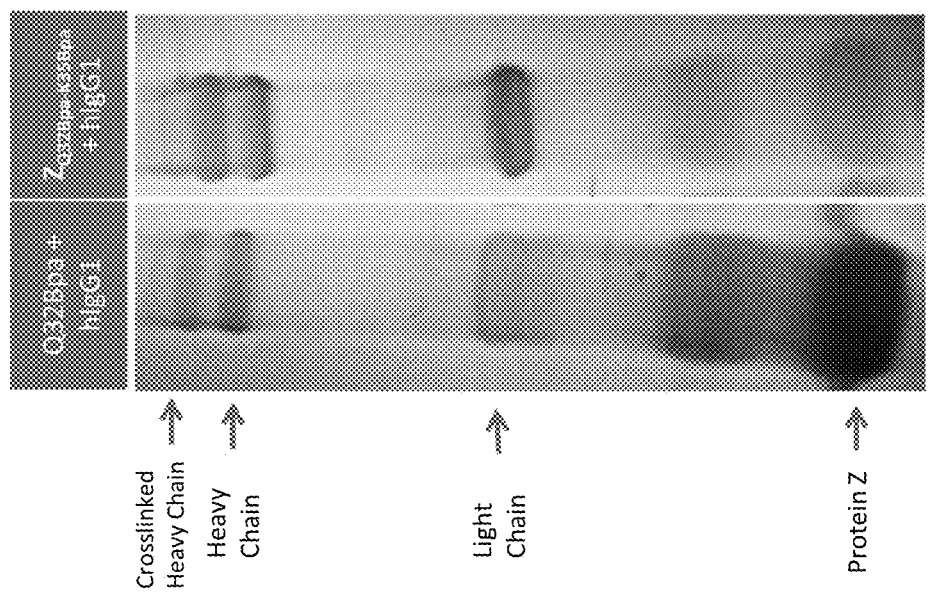
FIG. 24 shows crosslinking with Protein Z with Double Mutations $Z_{Q32\ Bpa\text{-}K35Bpa}$.

FIG. 24 shows crosslinking with Protein Z with Double Mutations $Z_{Q32Bpa-K35Bpa}$. A Protein Z variant containing two Bpas, located at Q32 and K35, ($Z_{Q32Bpa-K35Bpa}$) was crosslinked with human IgG (rituximab). The reactions were then run on a reducing SDS-PAGE gel and stained for proteins using Coomassie stain. The results show that no significant increased crosslinking is obtained with $Z_{Q32Bpa-K35Bpa}$ variant when compared to Q32Bpa variant.

Figure 25B:
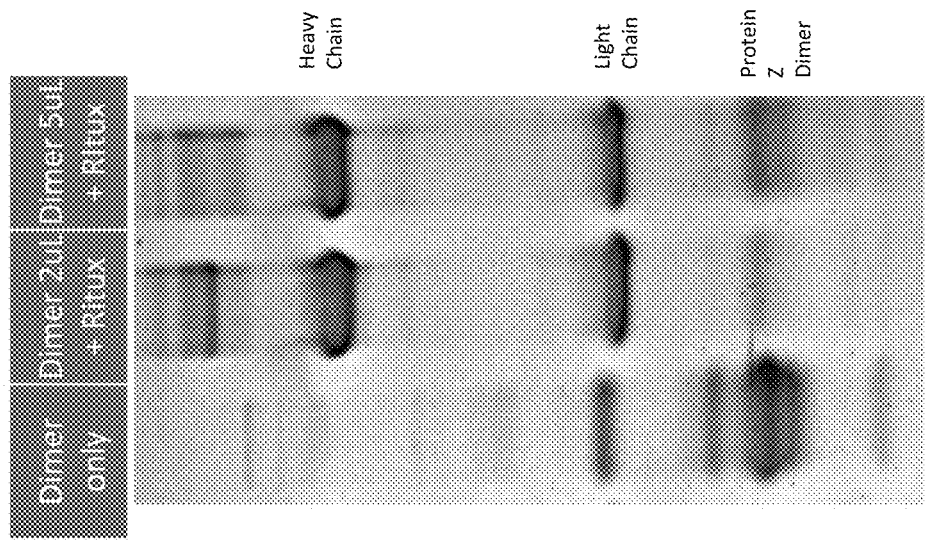
FIGS. 25A-25B.
Figure 25A:
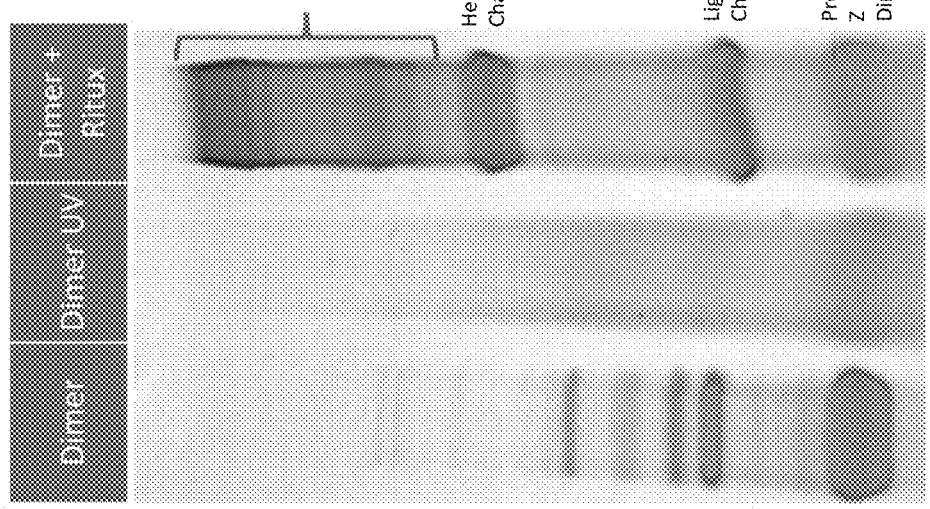

FIG. 25A shows self aggregation and high molecular aggregates and FIG. 25B shows WT Protein Z domain competing with Q32Bpa domain for binding to IgG. Two dimeric Protein Z variants, one containing two K35Bpa Protein Z domains separated by a GGS linker ($Z_{K35Bpa}$-GGSx7-$Z_{K35Bpa}$) and another containing a Q32Bpa and a wildtype Protein Z domains separated by a GGS linker ($Z_{WT}$-GGSx7-$Z_{Q32Bpa}$) were crosslinked with human IgG (rituximab). The reactions were then run on a reducing SDS-PAGE gel and stained for proteins using Coomassie stain. The results show that no significant increased crosslinking was obtained with either construct.

Crosslinking Monoclonal Antibodies in Ascites Solution

Figure 6:
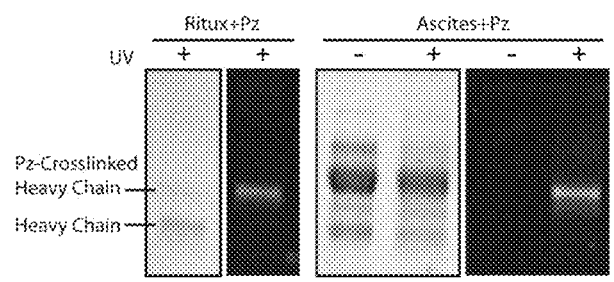
FIG. 6. Crosslinking of photoreactive Protein Z and IgG in ascites fluid. Photoreactive F13BPA Protein Z-AzFP conjugates that were incubated with rituximab or monoclonal anti-BSA IgG in ascites fluid were either mock or UV irradiated and analyzed via a reducing SDS-PAGE gel. Gels were imaged under white light and via fluorescence.

In order to highlight Protein Z's specific binding towards IgG, crosslinking was also performed with monoclonal antibodies in ascites fluid. AzFP-ligated Protein Z was directly incubated with ascites fluid containing anti-BSA antibodies. As a control, Protein Z was also incubated with purified rituximab. Both samples were then exposed to UV light and examined by reducing SDS-PAGE gel. In the gel, an additional fluorescent band was observed in both crosslinked samples at a slightly higher apparent molecular weight than the IgG heavy chain, indicative of Protein Z-crosslinking (FIG. 6). No other fluorescent band was observed in the UV exposed ascites fluid sample. Together, these findings suggest that even in a complex biological solution such as the ascites fluid, Protein Z's capacity to crosslink IgG is not only preserved but also remains Fc-specific.

B Cell Labeling Using Rituximab Targeted SPIO Nanoparticles

Figure 7:
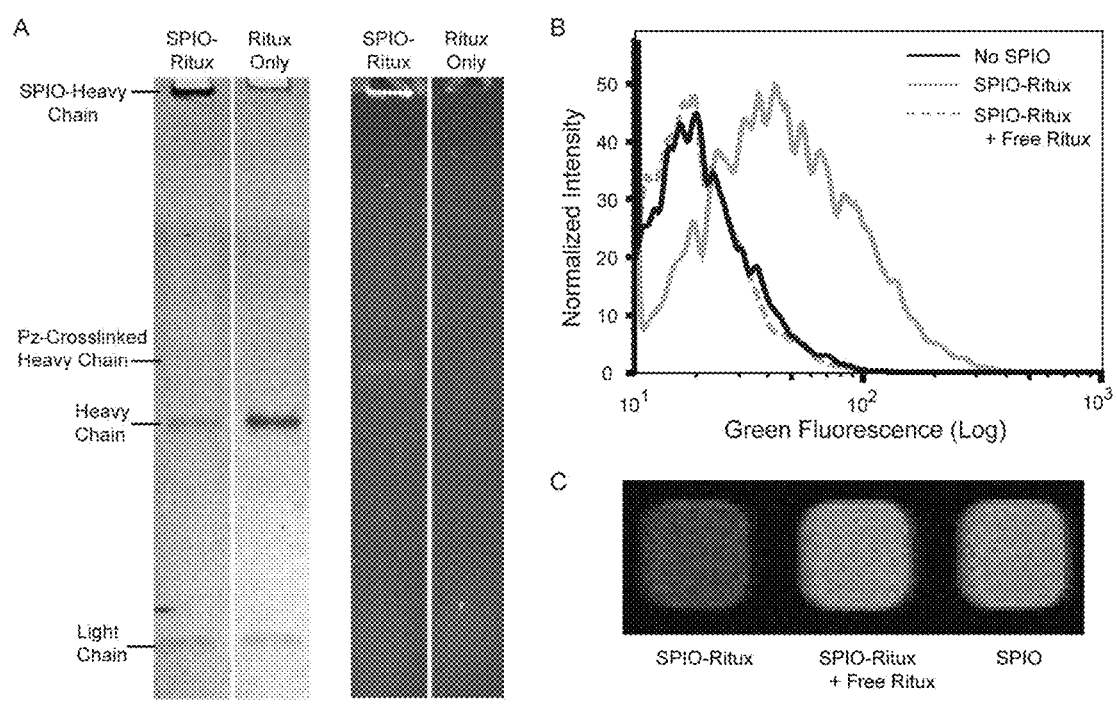
FIG. 7. Evaluation of B cell-targeted SPIO nanoparticles with site-specifically conjugated rituximab. (A) Photoreactive F13BPA Protein Z-AzFP was crosslinked to rituximab and conjugated onto ADIBO-functionalized SPIO (SPIO-Ritux). The SPIO-Ritux and rituximab alone were analyzed via a reducing SDS-PAGE gel. (B) Rituximab-conjugated SPIOs were used to label B cells in the presence and absence of excess free rituximab and the results analyzed using flow cytometry. (C) B cells were incubated with unmodified SPIO or SPIO-ritux in the presence or absence of excess free rituximab and T2*-weighted MR images of the respective cell pellets were acquired.
Figure 8:
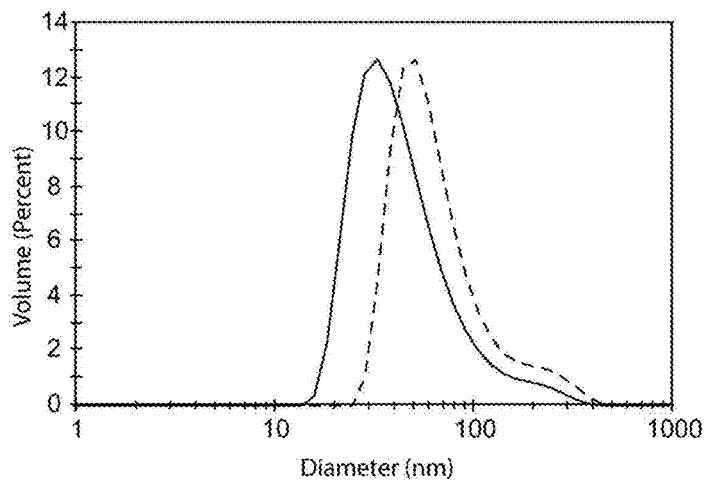
FIG. 8. Dynamic light scattering measurements of SPIO. The volume-weighted hydrodynamic diameter of unlabeled SPIO (solid) and SPIO-rituximab conjugates (dashed) were measured by dynamic light scattering. The measuring angle was 90°.

To underscore the versatility of Protein Z-crosslinked antibodies and their utility in nanotechnology applications, photoreactive Protein Z-AzFP was first crosslinked to rituximab and then site-specifically conjugated to ADIBO-functionalized SPIO nanoparticles (FIG. 1C: Conjugation). These rituximab-conjugated nanoparticles were analyzed by dynamic light scattering (DLS), which showed an increase in the hydrodynamic diameter following conjugation, from 51 nm for unlabeled nanoparticles to 76 nm for rituximab-conjugated-nanoparticles (FIG. 8). The correct conjugation was further confirmed via reducing SDS-PAGE gel. Since nanoparticles are too large to enter the gel matrix, the particles and their covalently conjugated Protein Z-heavy chain complex should not be able to migrate into the gel. This was indeed seen in FIG. 7A (fluorescent image), where the fluorescent Protein Z is seen to be stuck in bottom of the well containing rituximab-conjugated SPIO. Due to the reduction of disulfide bonds, the non-conjugated half of the IgG heavy chains and all of the light chains should be able to migrate normally into the gel. This effect is also seen in FIG. 7A (Coomassie image), where compared to the lane containing rituximab only sample, the lane containing rituximab-conjugated SPIO showed a selective reduction in the amount of heavy chains relative to light chains. It is also worth noting that since some rituximab molecules have both heavy chains crosslinked with a Protein Z, in cases where only one of the two Protein Z-linked heavy chains is immobilized on the SPIO, the non-immobilized Protein Z-heavy chain complex can still migrate into the gel. This is indicated by the fluorescent band that appears above the IgG heavy chain, in the lane containing rituximab-conjugated SPIO (FIG. 7A fluorescent image).

Figure 9:
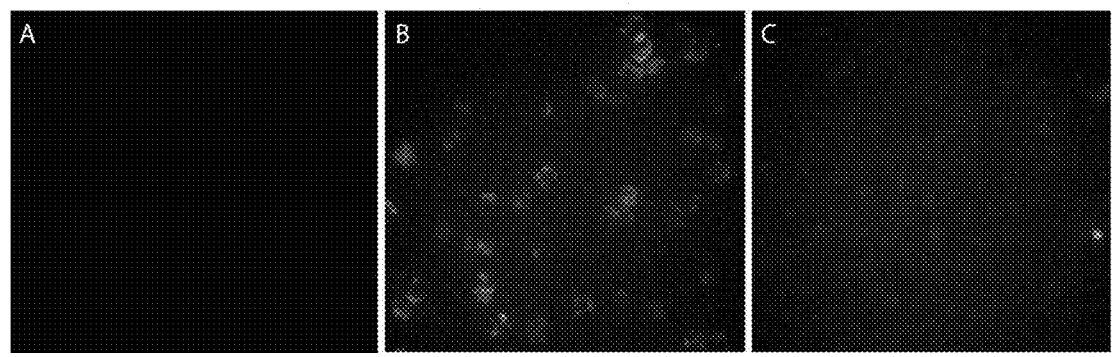
FIG. 9. Flourescent microscopy images of B cells. Fluorescent images of GA-10 B cells that were incubated with (A) unlabeled SPIO, (B) SPIO-rituximab conjugates, or (C) SPIO-rituximab conjugates in the presence of excess free rituximab.

To assay the binding capacity of rituximab-conjugated nanoparticles, the nanoparticles were used to label B-cells in vitro. Since each Protein Z carries a 5-FAM fluorophore, successful labeling of B cells can be established by flow cytometry (FIG. 7B) and fluorescence microscopy (FIG. 9). Upon treating B cells with rituximab-coated SPIO particles, there was a clear increase in the fluorescent signal. When free rituximab was used as a competitive inhibitor, the labeling was blocked, indicating the specificity of targeting.

Receptor-specific cell targeting was also confirmed using T2-weighted magnetic resonance (MR) imaging (FIG. 7C). B cell suspensions were imaged in a microplate following incubation with either rituximab-conjugated SPIO, in the presence or absence of excess free rituximab, or with non-functionalized SPIO. Consistent with the flow cytometry studies, B cells incubated with rituximab-conjugated SPIO exhibited much higher MR contrast (indicated by hypointense pixels), compared with B cells incubated with either non-targeted SPIO or targeted SPIO in the presence of a competitive inhibitor.

Given the tremendously diverse applications requiring antibody conjugates and the variability, non-uniformity, and/or low efficiency of existing conjugation methods, there is a clear need for an enabling technology that is simple, site-specific and broadly applicable. Here, we have shown that an engineered bacterial expression system can efficiently produce a recombinant "tri-functional" Protein Z-based IgG binding domain containing: 1. A photoactive moiety that can be used to crosslink IgG. 2. an azido moiety at the C-terminus that can be used to attach conjugates. 3. a fluorophore for imaging. This construct allows for site-specific antibody bioconjugations and is broadly applicable, due to Protein A's natural affinity towards a variety of IgG Fc regions.

BPA was selected as the photoreactive crosslinker because it has several favorable properties. Specifically, BPA's benzophenone group can be activated by long wavelength UV light (365 nm), which is not harmful to antibodies or other proteins. Additionally, even after being UV excited to its triplet state, benzophenone can relax back to its unreactive ground state if there are no abstractable hydrogen atoms in close proximity. This allows the photoreactive Protein Z to be produced and handled in ambient light conditions with low risk of photobleaching.

By using the Expressed Protein Ligation (EPL) technique, we were also able to easily introduce a fluorophore and an azide moiety onto the Protein Z during the protein purification step. The 5-FAM fluorophore provides a convenient means to visualize and track conjugated antibodies while the azido group allows further derivitization with a broad array of conjugates. Azide is a particularly attractive choice because it is a click chemistry moiety that is biocompatible, highly reactive and yet also highly specific. Pending user preference, other application-specific functions can also be easily incorporated into our Protein Z since the short EPL peptide that carries the functional groups can be easily synthesized. We have already successfully incorporated a terminal alkyne in place of the azido group and an Atto 740 near infrared dye in place of the 5-FAM fluorophore.

Lastly, since the reported Protein Z is produced recombinantly, it can be produced efficiently and in high yields. This makes this conjugation method readily accessible to a large number of researchers and scalable for commercial applications, especially given the ease of use and widespread availability of the E coli. expression system.

To demonstrate the applicability of our conjugation method, we utilized it to create targeted nanoparticles. While nanoparticles that are currently in clinical use (i.e. Doxil) mostly rely on the Enhanced Permeability and Retention effect (EPR) to accumulate in disease tissues, it is increasingly clear that in order to achieve more sensitive diagnosis, safer therapeutic index and more exquisite control of pharmacokinetics, targeting is required. Due to their limited surface area, nanoparticle avidity is particularly sensitive to poorly oriented antibodies generated by traditional conjugation methods. A versatile, Protein Z based site-specific conjugation method therefore can be used to improve the targeting capabilities of various targeted nanoparticle formulations.

In sum, the inventors have successfully demonstrated that a recombinantly expressed, photoactive Protein Z domain can be used to site-specifically and covalently conjugate IgGs onto nanoparticles. The conjugation method described herein is favorable for several reasons. 1. It is broadly applicable to a wide range of native full-length antibodies. 2. It conjugates IgGs at their Fc domains, hence avoiding steric hindrance or destruction of the antigen binding domain. 3. The mild yet versatile nature of our technique can be used for a wide range of numerous applications.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A conjugate composition comprising a variant of protein Z comprising a photoreactive crosslinker that permits specific binding to an immunoglobulin Fc region, wherein the variant of protein Z comprises an amino acid sequence about sixty-one amino acids in length and which has at least 80% identity to the sequence set forth in SEQ ID NO: 1 with the photoreactive crosslinker substituted for or introduced at F13, Q32, K35, N28, N23, or L17.

2. The composition of claim 1, wherein said immunoglobulin is IgG.

3. The composition of claim 1, wherein said photoreactive crosslinker is a UV-active non-natural amino acid.

4. The composition of claim 3, wherein said amino acid is benzoylphenylalaine (BPA).

5. The composition of claim 1, wherein said composition comprises a fusion protein comprising the variant of protein Z fused to an additional polypeptide.

6. The composition of claim 5, wherein said fusion protein further comprises a moiety for expressed protein ligation.

7. The composition of claim 6, wherein said moiety is an intein-MPB group or a sortase-His×6 group.

8. The composition of claim 1, wherein said variant of protein Z is attached to a peptide following an expressed protein ligation.

9. The composition of claim 8, wherein said peptide is attached to an additional polypeptide of interest via a crosslinker.

10. The composition of claim 8, wherein said peptide comprises a chemical moiety that permits chemical binding to a corresponding chemical group.

11. The composition of claim 10, wherein said chemical binding is click chemistry or maleimide chemistry.

12. The composition of claim 8, wherein said variant of protein Z is specifically attached in the proper orientation to a surface, polypeptide, a nanoparticle, or a drug via said click chemistry.

13. The composition of claim 9, wherein said additional polypeptide is a drug, an imaging agent, or a toxin.

14. A bacterial cell for recombinantly expressing the composition of claim 8.

15. A bacterial cell for recombinantly expressing the composition of claim 1.

16. A nanoparticle conjugate comprising the composition of claim 1.

17. A modified antibody complex comprising the composition of claim 1.

18. The modified antibody complex of claim 17, comprising a drug-antibody combination.

19. A method of imaging a biological sample, the method comprising the step of contacting said biological sample with the nanoparticle conjugate of claim 16, wherein said contacting permits imaging of said biological sample.

20. A method of imaging a biological sample, the method comprising the step of contacting a biological sample with said antibody complex of claim 17, wherein said contacting permits imaging of said biological sample.

21. The method of claim 19, wherein said biological sample is associated with a disease.

22. The method of claim 21, wherein imaging said biological sample permits diagnosing a disease.

23. The method of claim 21, wherein said biological sample is tissue, DNA, sperm, sera, blood, cerebrospinal fluid, or a biomarker.

24. A method of producing the conjugate composition of claim 1, the method comprising the step of recombinantly expressing said conjugate composition in a bacterial cell.

25. The composition of claim 4, wherein the variant is K35BPA or L17BPA.

* * * * *